United States Patent [19]

Mizuno et al.

[11] Patent Number: 5,081,021

[45] Date of Patent: Jan. 14, 1992

[54] DNA ENCODING HTNF VARIANTS EXHIBITING ENHANCED ACTIVITY

[76] Inventors: Den'ichi Mizuno, Okamoto-18, Kamakura, Kanagawa; Gen-Ichiro Soma, Higashi-Tamagawa 1-10-21, Setagaya, Tokyo, both of Japan

[21] Appl. No.: 10,692

[22] Filed: Feb. 4, 1987

[30] Foreign Application Priority Data

Feb. 4, 1986 [JP] Japan .................................. 61-21302
Feb. 7, 1986 [JP] Japan .................................. 62-24220

[51] Int. Cl.$^5$ ...................... C12P 21/00; C12P 21/02; C07H 15/12
[52] U.S. Cl. .................. 435/69.5; 435/320.1; 435/91; 536/27; 935/9; 935/11; 935/12; 935/13
[58] Field of Search ............... 435/68, 70, 91, 172.3, 435/253, 254, 255, 256, 320; 935/47, 48, 65; 536/27; 530/351

[56] References Cited

U.S. PATENT DOCUMENTS

| | | | |
|---|---|---|---|
| 4,532,207 | 7/1985 | Brewer et al. | 435/68 |
| 4,677,063 | 6/1987 | Mark et al. | 435/68 |
| 4,677,069 | 6/1987 | Mark et al. | 435/68 |
| 4,769,326 | 9/1988 | Rutter | 435/68 |

FOREIGN PATENT DOCUMENTS

| | | |
|---|---|---|
| 155549 | 2/1985 | European Pat. Off. |
| 168214 | 7/1985 | European Pat. Off. |
| 210588 | 7/1986 | European Pat. Off. |

OTHER PUBLICATIONS

*Annals New York Academy of Sciences*, (1975), vol. 249, pp. 134-135, "Properties of Bovine Thymosin", Hooper et al.
*Biochemical and Biophysical Research Communications*, (1985), vol. 132, pp. 100-109, "Detection of a Countertranscript in Promyelocytic . . . " Soma et al.
*Biochemistry*, (1978), vol. 17, pp. 1257-1267, "High--Pressure Liquid Chromatography in Polynucleotide Synthesis", Fritz et al.
*Gene*, (1985), vol. 34, p. 148, "Materials and Methods".
*Modern Chemistry*, (1985), pp. 34-38, Gendai Kagaku.
*Nucleic Acids Res*, (1981), vol. 10, pp. 7439-7448, "Silica Gel: An Improved Support for the Solid-Phase Phosphotriester Synthesis . . . " et al.
*Nature*, (1982), vol. 298, pp. 347-350, "Synthesis and Assembly of Hepatitis B Virus Surface Antigen Particles in Yeast", Valenzuela et al.
*Proc. Natl. Acad. Sci. U.S.A.*, (1983), vol. 80, pp. 1-5; "Expression of Hepatitis B Surface Antigen Gene in Yeast", A. Miyanohara, et al.
*Proc. Nat. Acad. Sci. U.S.A.*, (1975), vol. 72, pp. 3666-3670, "An Endotoxin-Induced Serum Factor That Causes Necrosis of Tumors", E. Carswell, et al.
*Science*, (1985), vol. 230, pp. 943-945, "Recombinant Human Tumor Necrosis Factor-a: Effects on Proliferation of Normal and Transformed Cells in Vitro", Sugarman.
*The Journal of Biological Chemistry*, (1985), vol. 260, "Human Tumor Necrosis Factor", B. Aggarwalt, et al., pp. 2345-2354.
Cancer Research 47, 145-149, Jan. 1, 1987, Biological Effects of Recombinant Human Tumor and Normal Cell Lines.
J. Biochem, 101, 919-925 (1987) Comparative Studies of the Biological Activities of Human Tumor Necrosis Factor and its Derivatives.
Journal of Biological Response Modifiers 7:587-595, 1988, Biological Activities of Novel Recombinant Tumor Necrosis Factor Having N-Terminal Amino Acid . . .

*Primary Examiner*—Robin L. Teskin
*Attorney, Agent, or Firm*—Oblon, Spivak, McClelland, Maier & Neustadt

[57] ABSTRACT

Novel DNA's encoding variants of TNF which comprise substitutions and/or deletions in the n-terminal portion of the TNF polypeptide resulting in enhanced cytotoxic activity are taught.

10 Claims, 12 Drawing Sheets

AAATTTAAAGTTTTGGTCTTGGGGGAGGATGGATGGAGGTGAAAGTAAGGGGGTATTTCTAG
GAAGTTTAAGGGTCTCAGCTTTTCTTTTCTCCTCCTTCAGGATCATCTTCTGAACCCCG
AGTGACAAGCCTGTAGCCCATGTGTAGGTAAGAGCTCTGAGGATGTGTCTTGGAACTTGGAGG
GCTAGGATTTGGGGATTGAAGCCCGGCTGATGGTAGGCAGAACTTGGAGACAATGTGAGAAGGA
CTCGCTGAGCTCAAGGGAAGGGTGGAGGAACAGCACCAGGCCTTAGTGGGATACTCAGAACGTCA
TGGCCAAGTGGGATGTGGGATGACAGAGACAGAGGACAGGAACCGGATGTGGGGTGGGCAGAGC
TCGAGGGCCAGGATGTGGAGAGTGAACCGACTCTCCTCTCCTCTCCCTCTCTCCC
TCCCTCCAGCAAACCCTCAAGCTGAGGGCAGCTCCAGTGGCTGAACCGCGGGCAATGCCCT
CCTGGCCAATGGCGTGGAGCTGAGAGATAACCAGCTGGTGGTGCCATCAGAGGGCCTGTACCTC
ATCTACTCCCAGGTCCTCTTCAAGGGCCAAGGCTGCCCCTCCACCCATGTGCTCCTCACCCACA
CCATCAGCCGCATCGCCGTCTCCTACCAGACCAAGGTCAACCTCTCTCTGCCATCAAGAGCCC
CTGCCAGAGGGAGACCCCAGAGGGGCTGAGGCCAAGCCTGACCTCAGCGCTGAGATCAATCGGCCGACTACCTCG
GGGTCTTCCAGCTGGAGAAGGGTGACCAGGTCTACTTTGGGATCATTGCCCTGTGAGGAGGACGAACATCCAA
ACTTTGCCGAGTCTGGGCAGGTCTCCCCTGCCCAATCCCTTATTACCCCTCCTTCAGACACCCTCAACCT
CCTTCCCAAACGCCTCCCCTGCCCCAATCCCTTATTACCCCTCCTTCAGACACCCTCAACCT
CTTCTGGCTCAAAAAGAGAATTGGGGGCTTAGGGTTGGAACCAAGCTTAGAACTTAAGCAAC
AAGACCACCTTCGAAACCTGGGATTCAGGATAGTGTGGCCTGCACAGTGAAGTGCTGGCAAC
CACTAAGAATTCAAACTGGGGCCTCCAGAACTCACTGGGGCCTACAGCTTTGATCCCTGACATC
TGGAATCTGGAGACAAGGGAGCCTTTGGTTCTGGCCAGAATGCTGCAG

*FIG. 4*

ATG ACC ATG ATT ACG AAT TCG AGC TCG CCC GGG GAT CCT CTA GAG TCG AGG GCC AGG ATG TGG
Met-Thr-Met-Ile-Thr-Asn-Ser-Ser-Pro-Gly-Asp-Pro-Leu-Glu-Ser-Arg-Ala-Arg-Met-Trp-

AGA GTG AAC CGA CAT GGC CAC ACT GAC TCT CCT CTC TCC CTC CCT CCA GCA AAC CCT
Arg-Val-Asn-Arg-His-Gly-His-Thr-Asp-Ser-Pro-Leu-Ser-Leu-Pro-Pro-Ala-Asn-Pro-

CAA GCT GAG GGG CAG CTC CAG TGG CTG AAC CGC CGG GCC AAT GCC CTC CTG GCC AAT GGC GTG
Gln-Ala-Glu-Gly-Gln-Leu-Gln-Trp-Leu-Asn-Arg-Arg-Ala-Asn-Ala-Leu-Leu-Ala-Asn-Gly-Val-

GAG CTG AGA GAT AAC CAG CTG GTG CCA TCA GAG GGC CTG TAC CTC ATC TAC CTC CAG GTC
Glu-Leu-Arg-Asp-Asn-Gln-Leu-Val-Pro-Ser-Glu-Gly-Leu-Tyr-Leu-Ile-Tyr-Ser-Gln-Val-

CTC TTC AAG GGC CAA GGC TGC CCC TCC ACC CAT GTG CTC CTC ACC CAC ACC ATC AGC CGC ATC
Leu-Phe-Lys-Gly-Gln-Gly-Cys-Pro-Ser-Thr-His-Val-Leu-Leu-Thr-His-Thr-Ile-Ser-Arg-Ile-

GCC GTC TCC TAC CAG ACC AAG GTC AAC CTC CTC TCT GCC ATC AAG AGC CCC TGC CAG AGG GAG
Ala-Val-Ser-Tyr-Gln-Thr-Lys-Val-Asn-Leu-Leu-Ser-Ala-Ile-Lys-Ser-Pro-Cys-Gln-Arg-Glu-

ACC CCA GAG GGG GCT GAG GCC AAG CCC ATC TGG TAT GAG CCC ATC TAT CTG GGA GGG CTC TTC CAG
Thr-Pro-Glu-Gly-Ala-Glu-Ala-Lys-Pro-Ile-Trp-Tyr-Glu-Pro-Ile-Tyr-Leu-Gly-Gly-Val-Phe-Gln-

CTG GAG AAG GGT GAC CGA CTC AGC GCT GAG ATC AAT CGG CCC GAC TAC CTC GAC TTT GCC GAG
Leu-Glu-Lys-Gly-Asp-Arg-Leu-Ser-Ala-Glu-Ile-Asn-Arg-Pro-Asp-Tyr-Leu-Asp-Phe-Ala-Glu-

TCT GGG CAG GTC TAC TTT GGG ATC ATT GCC CTG
Ser-Gly-Gln-Val-Tyr-Phe-Gly-Ile-Ile-Ala-Leu

*FIG. 5*

ATG TGG AGA GTG AAC CGA CAT GGC CAC ACT GAC TCT CCT CTC TCC CTC CCT CCA GCA
Met-Trp-Arg-Val-Asn-Arg-His-Gly-His-Thr-Asp-Ser-Pro-Leu-Ser-Leu-Pro-Pro-Ala-

AAC CCT CAA GCT GAG GGG CAG CTC CAG TGG CTG AAC CGC CGG GCC CTC CTT GCC AAT
Asn-Pro-Gln-Ala-Glu-Gly-Gln-Leu-Gln-Trp-Leu-Asn-Arg-Arg-Ala-Leu-Leu-Ala-Asn-

GGC GTG GAG CTG AGA GAT AAC CAG CTG GTG GTG CCA TCA GAG GGC CTG TAC CTC TCC
Gly-Val-Glu-Leu-Arg-Asp-Asn-Gln-Leu-Val-Val-Pro-Ser-Glu-Gly-Leu-Tyr-Leu-Ser-

CAG GTC CTC TTC AAG GGC CAA GGC TGC CCC TCC ACC CAT GTG CTC CTG ACC CAC ATC AGC
Gln-Val-Leu-Phe-Lys-Gly-Gln-Gly-Cys-Pro-Ser-Thr-His-Val-Leu-Leu-Thr-His-Thr-Ile-Ser-

CGC ATC GCC GTC TCC TAC CAG GTC AAC ATC CTC TCT GCC ATC AAG AGC CCC TGC CAG
Arg-Ile-Ala-Val-Ser-Tyr-Gln-Thr-Lys-Val-Asn-Leu-Leu-Ser-Ala-Ile-Lys-Ser-Pro-Cys-Gln-

AGG GAG ACC CCA GAG GGG GCT GAG GCC AAG CCC TGG TAT GAG CCC ATC TAT CTG GGA GGG GTC
Arg-Glu-Thr-Pro-Glu-Gly-Ala-Glu-Ala-Lys-Pro-Trp-Tyr-Glu-Pro-Ile-Tyr-Leu-Gly-Gly-Val-

TTC CAG CTG GAG AAG GGT GAC CGA CTC AGC GCT GAG ATC AAT CGG CCC GAC TAC CTC GAC TTT
Phe-Gln-Leu-Glu-Lys-Gly-Asp-Arg-Leu-Ser-Ala-Glu-Ile-Asn-Arg-Pro-Asp-Tyr-Leu-Asp-Phe-

GCC GAG TCT GGG CAG GTC TAC TTT GGG ATC ATT GCC CTG
Ala-Glu-Ser-Gly-Gln-Val-Tyr-Phe-Gly-Ile-Ile-Ala-Leu

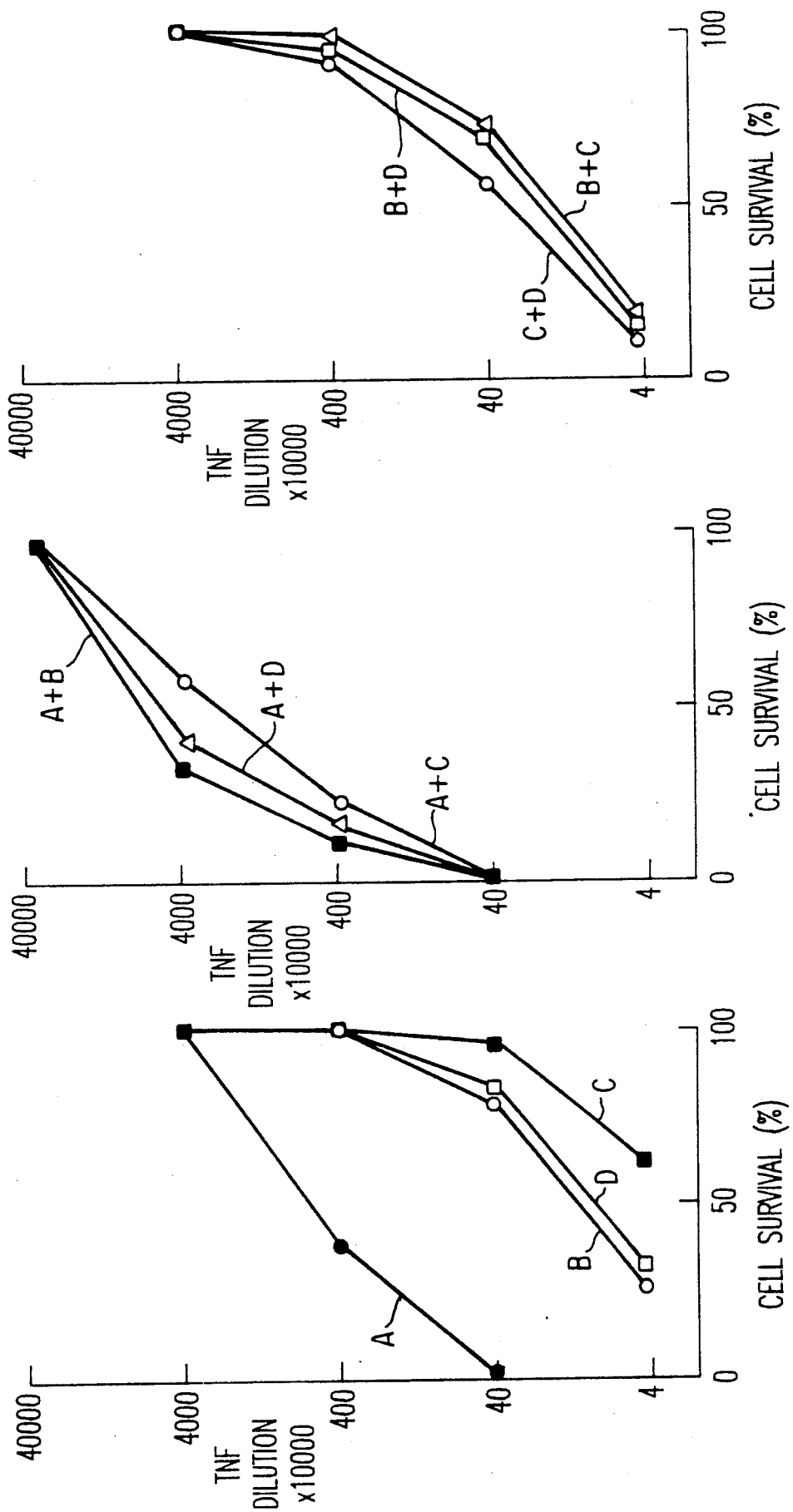

DNA ENCODING HTNF VARIANTS EXHIBITING ENHANCED ACTIVITY

DESCRIPTION

Cross-reference to Related Applications

Reference is made to application Ser. No. 891,279 now abandoned, filed by the same applicants as of the present application, entitled "Anti-Tumor Polypeptides and A Method of Preparing The Same"

FIELD OF THE INVENTION

This invention relates to DNAs. More particularly, it is concerned with DNAs coding anti-tumor polypeptides, plasmids possessing them, such polypeptides and processes for their preparation, and anti-tumor agents comprising said polypeptides.

DESCRIPTION OF THE PRIOR ART

TNF is a human anti-tumor polypeptide which is cytotoxic to mousefibroblast L-929, and which is obtained from human cell HL-60 (ATCC 240), as described in "The Journal of Biol. Chem.", 260, pp, 2345-2354, 1985. Most of the amino acid sequence of this polypeptide has been elucidated. Other polypeptides named TNF are known to be produced by *E. coli* which has been transformed with a certain recombinant plasmid (see "Nature", 312, pp. 724-729, Dec. 20/27, 1984, "Nature", 313, pp. 803-806, Feb. 28, 1985, and "Science", 228, pp. 149-154, Apr. 12, 1985)

However, the base sequence of the cloned DNA suggests that the latter polypeptides produced by the transformed *E. coli* are essentially the same as the TNF described in "The Journal of Biol. Chem.", 280 referred to above; the only apparent difference is that the TNF described in "Nature", 313 does not have the two N-terminal amino acids of said TNF, that is, valine and arginine.

BRIEF SUMMARY OF THE INVENTION

Accordingly, it is the object of the present invention to provide novel genes coding novel anti-tumor polypeptides and processes for their preparation, novel plasmids with said genes inserted therein, said polypeptides and processes for their preparation, and novel anti-tumor agents comprising said polypeptides.

BRIEF DESCRIPTION OF THE FIGURES

FIG. 4 represents a partial base sequence of said gene.

FIG. 5 shows the base sequence of the anti-tumor polypeptide gene possessed by p12$^{TNF}$x/p and the amino acid sequence of the polypeptide coded by said base sequence.

FIG. 6 shows the base sequence of the anti-tumor polypeptide gene possessed by pUC540$^{TNF}$x/p and the amino acid sequence of the polypeptide coded by said base sequence.

FIG. 7 shows the Xho-PstI fragment of the above genome gene.

FIG. 12 is a graph exhibiting the synergistic anti-tumor activity of the combined use of the anti-tumor polypeptides having the X and the corresponding other anti-tumor polypeptides without the X, both being within the scope of the present invention.

DETAILED DESCRIPTION OF THE INVENTION

Figure 1:
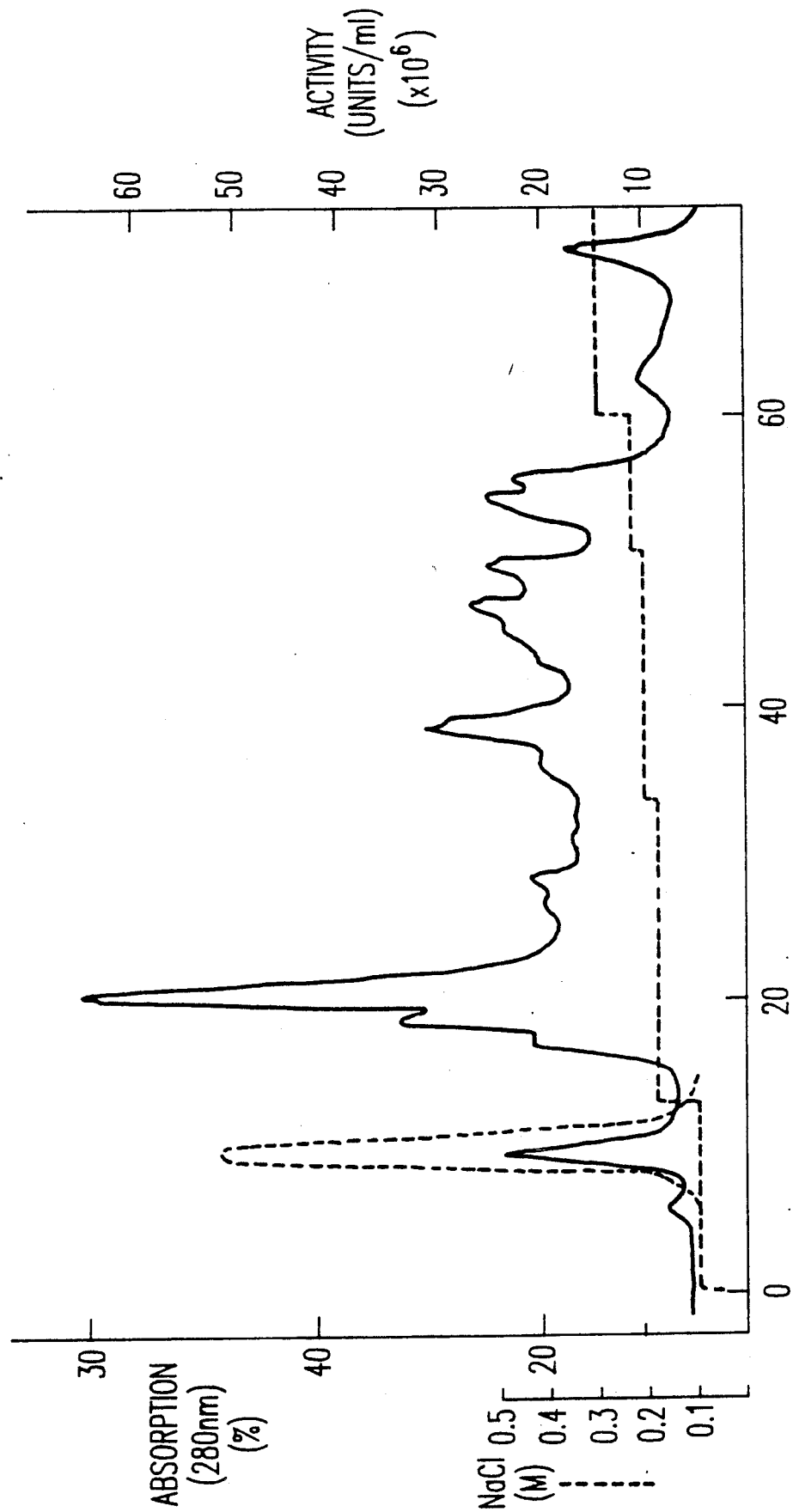
FIG. 1 is a graph showing the NaCl concentration which allows the anti-tumor polypeptide produced in Example 1 to elute in the course of its purification by the second FPLC of the mixture containing said anti-tumor polypeptide which is separated from THP-1 cells.

According to the present invention, there are provided DNAs coding the following amino acid sequence:

X—X'—Ala—Asn—Pro—Gln—Ala—Glu—Gly—Gln—Leu—
Gln—Trp—Leu—Asn—Arg—Arg—Ala—Asn—Ala—Leu—Leu—
Ala—Asn—Gly—Val—Glu—Leu—Arg—Asp—Asn—Gln—Leu—
Val—Val—Pro—Ser—Glu—Gly—Leu—Tyr—Leu—Ile—Tyr—
Ser—Gln—Val—Leu—Phe—Lys—Gly—Gln—Gly—Cys—Pro—
Ser—Thr—His—Val—Leu—Leu—Thr—His—Thr—Ile—Ser—
Arg—Ile—Ala—Val—Ser—Tyr—Gln—Thr—Lys—Val—Asn—
Leu—Leu—Ser—Ala—Ile—Lys—Ser—Pro—Cys—Gln—Arg—
Glu—Thr—Pro—Glu—Gly—Ala—Glu—Ala—Lys—Pro—Trp—
Tyr—Glu—Pro—Ile—Tyr—Leu—Gly—Gly—Val—Phe—Gln—
Leu—Glu—Lys—Gly—Asp—Arg—Leu—Ser—Ala—Glu—Ile—
Asn—Arg—Pro—Asp—Tyr—Leu—Asp—Phe—Ala—Glu—Ser—
Gly—Gln—Val—Tyr—Phe—Gly—Ile—Ile—Ala—Leu wherein X is a hydrogen atom or a peptide the type and number of which may be chosen as desired, and X' represents a peptide having 1-39 amino acid residues.

In the amino acid sequence given above, the portion from the Ala located downstream of the X' to the last Leu is the same as the amino acid sequence of the hitherto known fourth exon of TNF except that the fourth exon lacks the guanine consisting of the first Ala.

The DNAs of the present invention may be synthesized chemically on the basis of processes described in "Nucleic Acids Res.", 10, pp. 7439-7448 (1981), "Biochemistry", 17, pp. 1257-1267 (1978) etc. As an example, a process for preparing DNAs of the present invention starting with the genome DNA of human acute monocytic leukemia cell THP-1 will be detailed in examples given later. In addition, in case the base sequence of the nineteenth amino acid alanine is GCG, the base sequence may be cleaved just before the base sequence being the same as that of the fourth exon of TNF by the use of restriction enzyme NruI (TCGCGA) to introduce some other desired base sequences. This introduction is very useful.

Some embodiments of the peptides represented by X' are listed below.

(1) Initiation codon Met:

(2) Met-Val-Ser-Ser-Arg-Thr-Pro-Ser-Asp-Lys-Pro-Val-Ala-His-Val-Val;
(3) Met-Val-Arg-Ser-Ser-Arg-Thr-Pro-Ser-Asp-Lys-Pro-Val-Ala-His-Val-Val;
(4) Met-Val Arg-Ser-Cys-Thr-Arg-Thr-Pro-Ser-Arg-Lys-Pro-Val-Ala-His-Val-Val;
(5) Met-Val-Arg-Ser-Cys-Thr-Arg-Thr-Pro-Ser-Arg-Lys-Ala-Val-Ala-His-Val-Val;
(6) Met-Val-Arg-Ser-Cys-Thr-Arg-Thr-Pro-Ser-Pro-Lys-Pro-Val-Ala-His-Val-Val;
(7) Met-Val-Arg-Ser-Cys-Thr Arg Thr-Pro-Ser-Pro-Lys-Ala-Val-Ala-His-Val-Val;
(8) Met-Val-Arg-Ser-Cys-Thr-Pro-Thr-Pro-Ser-Arg-Lys-Pro-Val-Ala-His-Val-Val;
(9) Met-Val-Arg-Ser-Cys-Thr-Pro-Thr-Pro-Ser-Arg-Lys-Ala-Val-Ala-His-Val-Val;
(10) Met-Val-Arg-Ser-Cys-Thr-Pro-Thr-Pro-Ser-Pro-Lys-Pro-Val-Ala-His-Val-Val;
(11) Met-Val-Arg-Ser-Cys-Thr-Pro-Thr-Pro-Ser-Pro-Lys-Ala-Val-Ala-His-Val-Val;
(12) Met-Val-Arg-Ser-Ser-Thr-Arg-Thr-Pro-Ser-Arg-Lys-Pro-Val-Ala-His-Val-Val;
(13) Met-Val-Arg-Ser-Ser-Thr-Arg-Thr-Pro-Ser-Arg-Lys-Ala-Val-Ala-His-Val-Val;
(14) Met-Val-Arg-Ser-Ser Thr-Arg-Thr-Pro-Ser-Pro-Lys-Pro-Val-Ala-His-Val-Val;
(15) Met-Val-Arg-Ser-Ser-Thr-Arg-Thr-Pro-Ser-Pro-Lys-Ala-Val-Ala-His-Val-Val;
(16) Met-Val-Arg Ser Ser Thr Pro-Thr-Pro-Ser-Arg Lys-Pro-Val-Ala-His-Val-Val;
(17) Met-Val-Arg-Ser-Ser-Thr-Pro-Thr-Pro-Ser-Arg-Lys-Ala-Val-Ala-His-Val-Val;
(18) Met-Val-Arg-Ser-Ser-Thr-Pro-Thr-Pro-Ser-Pro-Lys-Pro-Val-Ala-His-Val-Val;
(19) Met-Val-Arg-Ser-Ser-Thr-Pro-Thr-Pro-Ser-Pro-Lys-Ala-Val-Ala-His-Val-Val;
(20) Met-Val-Lys-Ser-Cys-Thr-Arg-Thr-Pro-Ser-Arg-Lys-Pro-Val-Ala-His-Val-Val;
(21) Met-Val-Lys-Ser-Cys-Thr-Arg-Thr-Pro-Ser-Arg-Lys-Ala-Val-Ala-His-Val-Val;
(22) Met-Val-Lys-Ser-Cys-Thr-Arg-Thr-Pro-Ser-Pro-Lys-Pro-Val-Ala-His-Val-Val;
(23) Met-Val-Lys-Ser-Cys-Thr-Arg-Thr-Pro-Ser-Pro-Lys-Ala-Val-Ala-His-Val-Val;
(24) Met-Val-Lys-Ser-Cys-Thr-Pro-Thr-Pro-Ser-Arg-Lys-Pro-Val-Ala-His-Val-Val;
(25) Met-Val-Lys-Ser-Cys-Thr-Pro-Thr-Pro-Ser-Arg-Lys-Ala-Val-Ala-His-Val-Val;
(26) Met-Val-Lys-Ser-Cys-Thr-Pro-Thr-Pro-Ser-Pro-Lys-Pro-Val-Ala-His-Val-Val;
(27) Met-Val-Lys-Ser-Cys-Thr-Pro-Thr-Pro-Ser-Pro-Lys-Ala-Val-Ala-His-Val-Val;
(28) Met-Val-Lys-Ser-Ser-Thr-Arg-Thr-Pro-Ser-Arg-Lys-Pro-Val-Ala-His-Val-Val;
(29) Met-Val-Lys-Ser-Ser-Thr-Arg-Thr-Pro-Ser-Arg-Lys-Ala-Val-Ala-His-Val Val;
(30) Met-Val-Lys-Ser-Ser-Thr-Arg-Thr-Pro-Ser-Pro-Lys-Pro-Val-Ala-His-Val-Val;
(31) Met-Val-Lys-Ser-Ser-Thr-Arg-Thr-Pro-Ser-Pro-Lys-Ala-Val-Ala-His-Val-Val;
(32) Met-Val-Lys-Ser-Ser-Thr-Pro-Thr-Pro-Ser-Arg-Lys-Pro-Val-Ala-His-Val-Val;
(33) Met-Val-Lys-Ser-Ser-Thr-Pro-Thr-Pro-Ser-Arg-Lys-Ala-Val-Ala-His-Val-Val;
(34) Met-Val-Lys-Ser-Ser-Thr-Pro-Thr-Pro-Ser-Pro-Lys-Pro-Val-Ala-His-Val-Val;
(35) Met-Val-Lys-Ser-Ser-Thr-Pro-Thr-Pro-Ser-Pro-Lys-Ala-Val-Ala-His-Val-Val;
(36) Met-Val-Arg-Ser-Cys-Thr-Arg-Thr-Arg-Ser-Arg-Lys-Phe-Val-Ala-His-Val-Val; and
(37) Met-Val-Arg-Ser-Ser-Thr-Arg-Thr-Arg-Ser-Arg-Lys-Phe-Val-Ala-His-Val-Val.

In order to obtain an anti-tumor polypeptide using the DNAs of the present invention, the latter are incorporated into an appropriate vector DNA in an expressible manner, and the thus-obtained recombinant DNA is used to transform host organisms including animal cells, yeasts, *B. subtilis, E. coli.* and the like to induce the expression.

In order to incorporate a DNA of the present invention into a vector DNA in an expressible manner, as is well known, the DNA of the present invention is incorporated downstream of the Shine-Dalgarno sequence (hereunder referred to as the SD sequence) of a vector DNA possessing a promotor sequence (being usually downstream of an operator sequence) and the SD sequence which is located downstream of the promotor sequence. Alternatively, first the DNA of the present invention is incorporated into a vector DNA, and then a promotor sequence (usually together with an operator sequence) and the SD sequence are inserted upstream thereof. Processes for expression of genetic information of an exogenous gene by techniques using recombinant DNA are described generally in "Techniques for utilizing gene recombinant (4)", 1983, Science Forum; "Molecular Cloning", 1982, Cold Spring Harbor Lab.; "Introduction into cells and expression of recombinant genes", 1983, Kyoritsu Shuppan Cor.; etc.

The case where *E. coli* is used as the host will be illustrated in Example 1.

Alternatively, in case yeast is used as the host, the genetic information of the DNAs of the present invention can be expressed as described hereunder.

Plasmid vector pMA56 with a promotor for alcohol dehydrogenase (ADHI) incorporated therein ("Nature", 298, pp. 347–350, 1982) has an EcoRI site downstream of the promotor. Thus, the DNA of the present invention may be recovered as BamHI/PstI fragment from, for example, pUC540$^{TNF}$21/22, pUC540$^{TNF}$69/70, pUC540$^{TNF}$72/73, or pUC540AMCT-1 as described in Example 2 or 3, and then may be inserted into pMA56 at the EcoRI site downstream of the ADHI promotor thereof using EcoRI/BamIII linker and PstI/EcoRI linker to be controlled by the ADHI promotor, thereby expressing the genetic information in yeast.

Further, as repressible acidic phosphatase (PH05) promotor—having pAM82 ("Proc. Natl. Acad. Sci. U.S.A.", 80, pp. 1–5, 1983) has an XhoI site downstream of the PH05 promotor, the DNA of the present invention may be recovered as a BamHI/PstI fragment from, for example, pUC540$^{TNF}$21/22, pUC540$^{TNF}$69/70, pUC540$^{TNF}$72/73, or pUC540AMCT-1 as described in Example 2 or 3, and then may be inserted into pMA56 at its XhoI site downstream of the PH05 promotor thereof using BamHI/XhoI linker and PstI/XhoI linker to be controlled by PH05 promotor, thereby making the expression of the genetic information possible in yeast.

*B. subtilis* may also be employed as the host as follows to express the genetic information of DNAs of the present invention.

pTUB285 having an α-amylase promotor which is originally possessed by *B. subtilis* Marburs strain ("Gene", 34, p. 148, 1985) has a HincII site downstream of the promotor and a signal peptide. Thus, the DNA of the present invention may be recovered as BamHI/PstI fragment from, for example, pUC540$^{TNF}$21/22, pUC540$^{TNF}$69/70, pUC540$^{TNF}$72/73, or pUC5-40AMCT-1 as described in Example 2 or 3, and then may be inserted into pTUB285 at its HincII site using HincII/BamHI linker and HincII/PstI linker to be controlled by the α-amylase promotor to express the genetic information in *B. subtilis*. The anti-tumor polypeptide produced by the thus-transformed host cells may be separated and purified as follows.

The host cells are collected by, for example, centrifugation, and then crushed by treatment with ultrasonic waves or lysozyme. Here a hypotonic solution is used, and in some cases coexistence of a surfactant such as SDS or guanidine HCl may produce a better result. The crushed cell-containing solution is subjected to centrifugation to provide a supernatant.

The thus-prepared supernatant containing the anti-tumor polypeptide may be purified according to any conventional method of purifying proteins. That is, the supernatant may be subjected to purification by ion exchange chromatography using a basic anion exchanger, salting out, dialysis, gel filtration, hydrophobic chromatography, high performance molecular sieve chromatography, electrophoresis, etc., in the given order or by any desired combination of these methods.

For example, for purification of TNF-1, 2, or 3 from THP-1 cells, the basic anion exchanger is preferred to be DEAE-Sephadex A-25 or A-50, Sepharose CL-6B, or DEAE-Sephamil (all made by Pharmacia AB), but any other diethylamino, aminoethyl, or quaternary-aminoethyl group-containing anion exchanger may be used. Preferable embodiments of the buffer solution available for use include Tris-HCl and phosphate buffer solutions at pH 6.6–9.0. Any of these buffer solutions may be used at a low concentration of about 0.05M to dilute the culture containing the anti-tumor polypeptide to a saline concentration of 0.1M or less, and then the resulting solution is contacted with an anion exchanger which adsorbs the anti-tumor polypeptide. The elution of the anti-tumor polypeptide is carried out with a saline solution containing 0.1–0.2M of NaCl or KCl. The anti-tumor polypeptide is eluted at a saline concentration of about 0.2. The contact with the anion exchanger is preferably conducted by a column process, but a batch process may be employed if the contact is conducted on a large scale.

Before anion exchange chromatography is carried out, the solution is preferably pre-treated with an ultrafiltration membrane for removal of lower molecular materials, thereby improving the purification efficiency.

The solution resulting from the anion exchange chromatography is subjected to dialysis and concentration followed by gel filtration. Embodiments of carriers for the gel filtration include Sephadex G-75 and G-100 (manufactured by Pharmacia AB), Sephacryl S-200 (manufactured by Pharmacia AB), Biogel P-100 (manufactured by Biorad), and Toyo Pearl HW-50 and HW-55 (manufactured by Toyo Soda Corp.). The buffer solution intended for use in the gel filtration may be a Tris-HCl or phosphate buffer solution. To prevent adsorption it is desired that 0.2–0.5M of a saline such as NaCl be added to the solution.

Alternatively, the anti-tumor polypeptide active solution may be purified by hydrophobic chromatography. Here, Butyl-Toyo Pearl 650 or the like may be used as the carrier, and a saline such as ammonium sulfate or NaCl is employed to elute the anti-tumor polypeptide.

The anti-tumor polypeptide-containing solution purified by gel filtration or hydrophobic chromatography is then subjected to fast protein exchange chromatography using a Pharmacia FPLC (Fast Protein, Peptide, Polynucleotide, Liquid Chromatography) system to provide a purified sample.

The conditions for the fast protein anion exchange chromatography are the same as for the ion exchange chromatography using a carrier such as DESE-Sepharose mentioned previously.

Any of the polypeptides of the present invention may be purified in the same manner as described above. Namely, a solution containing crushed cells which contain the polypeptide is treated by ion exchange chromatography using a basic ion exchanger, salting out, dialysis, gel filtration, hydrophobic chromatography, high performance molecular sieve chromatography, electrophoresis, etc. in the order given here or by any desired combination of these methods.

The polypeptides of the present invention are of course highly cytotoxic to L-929 cells which have been observed to be sensitive to the hitherto known TNF. In addition, the polypeptides of the present invention are believed to be remarkably cytotoxic even to T-24 cells to which the prior art TNF has been reported to be thoroughly insensitive ("Science", 230, pp. 943–945, issued on Nov. 22, 1985). This cytotoxicity is believed to increase if the proportion of the number of the net basic amino acid residues to the number of all the amino acid residues constituting X and X', but excluding the initiation codon Met, is more than about 14.3%. Here, the number of the net basic amino acid residues is calculated by subtracting the number of acidic amino acid residues from the number of all the basic amino acid residues, and histidine is not deemed to be a basic amino acid. The cytotoxicity is believed to increase more if said proportion is about 20–50%. Furthermore, some of the polypeptides of the present invention have been observed to be remarkably cytotoxic to primary culture cells obtained from metastasis lesions of patients suffering from striated muscle tumors originating in ductus Mulleri and reported to be resistant to all chemotherapic agents. It has also been found that the anti-tumor activity synergistically increases if the polypeptide where X is a hydrogen atom, and X' is the above embodiment (1) is used in combination with another polypeptide where X represents Met-Arg-Ile-Arg, and X' is any of the above embodiments (1), (2) and (3), or a polypeptide of the present invention where X is a peptide is used in combination with another polypeptide of the present invention where X is a peptide.

The polypeptides of the present invention may be qualitatively and quantitatively analyzed as follows:

CYTOTOXICITY TO L-929 CELLS

L-929 cells ("Proc. Natl. Acad. Sci. U.S.A.", 72, pp. 3666–3670, 1983) are cultured in Eagles' Minimum Essential Medium (hereunder referred to only as MEM) with 5% of fetal calf serum (hereunder referred to only as FCS) added thereto until 100 μl of the medium contains $8 \times 10^4$ cells, and then the cells are grown in a flat-bottomed plate having 96 wells. The growth conditions are 2 hours at 37° C. in the presence of 5% $CO_2$, and 100% $H_2O$, and the procedures may be the same as for the conventional cell culture. Actinomycin D is then added in the medium to a final concentration of 1 μg/ml, and the volume of the culture solution is adjusted to 150 μl. Immediately thereafter 50 μl of the sample diluted appropriately with MEM medium is added to the culture solution. Here, $ED_{50}$ may be determined by adjusting the dilution appropriately. The L-929 cells having a final volume of 200 μl are cultured for an additional 18 hours under the same conditions as described above. In order to determine the cell necrosis activity, first the whole medium is removed followed by addition of 2% of a methyl alcoholic solution containing 0.2% of crystal violet for fixation staining. Crystal violet stains all the eukaryotic cells, but does not stain those cells left in the bottom of the flask as the result of necrosis, so the cell necrosis activity may be determined directly. The staining degree is measured on the basis of adsorption at $\Omega\eta_{609nm}$, and is compared with that of a control to determine the cell necrosis activity. This activity is defined as follows.

The dilution of the sample which allows the survival of 50% of L-929 cells (N) is determined. Rabbit TNS is used as the control, and its activity n (units/ml) is determined using $2.4 \times 10^6$ units/mq/ml of human TNF. The dilution which provides an $ED_{50}$ of rabbit TNS is determined.

The activity of the sample (units/ml) is calculated by the equation $N/C \times n$.

The cytotoxicity to A549 (lung carcinoma). LS174T (colon carcinoma) or WiDr (colon carcinoma) is determined substantially in the same manner as set out above.

CYTOTOXICITY TO T-24 CELLS

The subject toxicity is determined by the crystal violet (0.2%) staining method 24 hours after addition of polypeptides of the present invention or on the basis of the degree of suppression on intake of $^3$H-thymidine.

Hereunder, the present invention will be explained in more detail with reference to examples and experiments.

EXAMPLE 1

(1) Purification on TNF-1, 2 or 3 from THP-1 Cells

Two hundred liters of a PRM-1640 aseptic medium containing 5% FCS were charged into a 300 l culture tank, and THP-1 cells were suspended in the medium in such a manner that the cell content became $2 \times 10^5$/ml. The resulting suspension was cultured at 37° C. for 4 days, and the resulting culture solution was subjected to centrifugation to collect THP-1 cells aseptically. These cells were moved to 200 l of a serum-free RPMI-1640 medium placed in another culture tank followed by addition of 100 ng/ml of TPA thereto.

The solution was cultured under aseptic conditions at 37° C. for 5 days with gentle stirring (induction). The thus-prepared culture solution was subjected to centrifugation to separate and remove the cells, thereby collecting a supernatant having 100 units/ml of anti-tumor polypeptide activity. This supernatant was concentrated ten times with an ultrafiltration membrane (HVLP OHV20 manufactured by Millipore Corp.). Solid ammonium sulfate (65% saturation) was added to the resulting concentrated solution and dissolved therein to precipitate proteins. The precipitate was collected by centrifugation (at 1000 r.p.m. for 20 minutes), and then dissolved in a small quantity of 0.05M Tris-HCl buffer solution (pH 7.7). Then, the resulting solution was dialyzed against the same type buffer solution (5° C., 24 hrs.). The same quantity of the same type buffer solution was added to the inner solution which was then charged into a DEAE-Toyo Pearl M650 column (5 × 40 cm) previously equilibrated with the same type buffer solution. The column was washed with 1.0 l of the same type buffer solution followed by elution with the same type buffer solution containing 0.2M of NaCl.

Two liters of anti-tumor polypeptide active fractions were a collected and subjected to ammonium sulfate fractionation (40-50% saturation fraction), the resulting ammonium sulfate precipitate was dissolved in a small quantity of water, and the aqueous solution was sufficiently dialyzed against the same type buffer solution (5° C., 24 hrs.).

A 40% saturated solution of ammonium sulfate was added to and dissolved in the dialysis inner solution which was then subjected to centrifugation to remove insoluble matter, and then subjected to hydrophobic chromatography at a rate of 2.0 ml/min. using a Butyl-Toyo Pearl 650S column (2.5 × 30 cm) previously equilibrated with a 0.05M Tris-HCl buffer solution containing ammonium sulfate at 40% saturation. Then, anti-tumor polypeptide active fractions were collected and dialyzed against a 0.05M Tris-HCl buffer solution (pH 7.8).

The dialysis inner solution was charged into a Mono QHR 5/5 column (fast protein anion exchange column manufactured by Pharmacia AB) previously equilibrated with 50 mM of Tris-HCl buffer solution (pH 8.5), washed with the same type buffer solution, and then subjected to gradient elution where the NaCl concentration was successively increased to 0.1, 0.15, 0.2, and 0.3M to elute anti-tumor polypeptide active substances. The anti-tumor polypeptide fractions were eluted with 0.2M of NaCl and then purified to a specific activity of $6.25 \times 10^6$ units/mg protein. The fractions were purified 5 to 15 times in this step, and the recovery was 80% or more.

The thus-collected active fractions were treated with Pharmacia FPLC (Fast Protein, Peptide, Polynucleotide, Liquid Chromatography) system using a Mono Q HR5/5 column under the same conditions as described above. The elution pattern observed in this second FPLC is shown in FIG. 1 of the drawings. In FIG. 1, the vertical axis represents absorption at 280 nm (%), while the horizontal axis represents elution time (min.). As is clear from the drawing, the anti-tumor polypeptide active portions were eluted with 0.1M of NaCl, and this result agreed well with the peak at 280 nm. These active fractions were collected, dialyzed against pure water, and then lyophilized to provide 200 μg of a purified sample. The specific activity of this sample was $1 \times 10^7$ units/mg protein. Next, this protein was subjected to Mono Q column chromatography with a Pharmacia FPLC system. The elution was carried out under the conditions given in Table 1.

TABLE 1

| Time (min.) | Solution A (50 mM Tris -HCl, pH 8.5) | Solution B (1M NaCl/ 50 mM Tris-HCl, pH 8.5 |
|---|---|---|
| 0-5 | 100% | 0% |
| 5 | 95% | 5% |
| 35 | 90% | 10% |
| 35-45 | 90% | 10% |

Under these eluted conditions fractions corresponding to the three peaks eluted with a retention time of 35, 36 and 37.8 minutes, respectively (hereunder, those fractions corresponding to the three peaks are referred to only as TNF-1, TNF-2 and TNF-3, respectively). The respective fractions were subjected to chromatography again under the same conditions as described above for further purification. All of the fractions were proved to be simple proteins by the procedures given below.

(2) Procedures of TNF-1, 2 and 3

Figure 2:
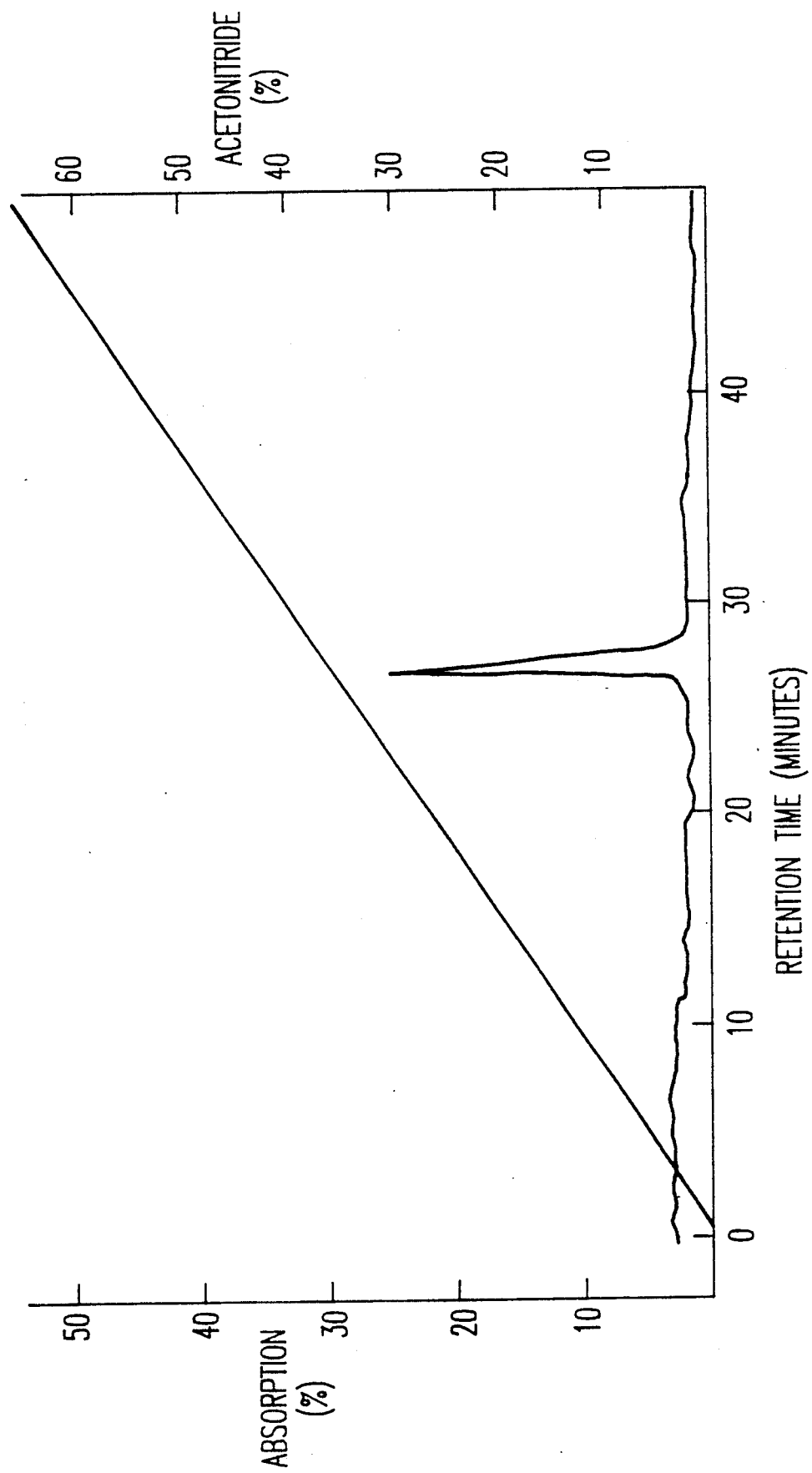
FIG. 2 is a graph showing the elution pattern of TNF-1 in reverse phase FPLC.

Samples of the respective fractions were subjected to reverse phase FPLC using a Pro-FPC HR 5/2 (C4 reverse phase carrier manufactured by Pharmacia AB) column. The elution was conducted using 0.1% of trifluoroacetic acid as the developer and increasing the acetonitrile concentration from 0% to 70% linearly with respect to time. Of the three elution patterns only that of TNF-1 is shown in FIG. 2. TNF-1 polypeptide was eluted at an acetonitrile concentration of around 36%, and no other peaks of proteins were observed. TNF-2 and TNF-3 also produced substantially the same effects. Thus, it can be concluded that TNF-1, TNF-2 and TNF-3 are all simple substances in view of their behavior in reverse phase FPLC.

Then, the same samples were subjected to SDS-polyacryl amide gel electrophoresis (hereunder referred to as SDS-PAGE). That is, using a Slab electrophoresis unit manufactured by Biorad Corp. (Protein, 16 cm), the sample was charged into 15.0% polyacryl amide gel containing 0.1% of SDS, and the electrophoresis was conducted at a constant current of 20 mA. Then the detection of proteins was attempted by silver impregnation. In each case, only a single band was detected at the position of 17.4 Kd, and no other protein band was found. Accordingly, TNF-1, TNF-2 and TNF-3 all proved to be single proteins in view of the behavior in SDS-PAGE. All the isoelectric points (pI) of these protein samples were determined to be 5.7 according to the polyacryl amide gel isoelectric electrophoresis using Ampholine polyacryl amide gel manufactured by LKB Produkter AB.

Next, the amino acid sequence of these three anti-tumor polypeptides were determined by analysis of about 10 µg of each of them starting with the N-terminal using an amino acid sequence analyzer (Model 470A) manufactured by Applied Biosystems Inc. As results, the N-terminal amino acid sequence of TNF-1, TNF-2 and TNF-3 were found to be as follows:

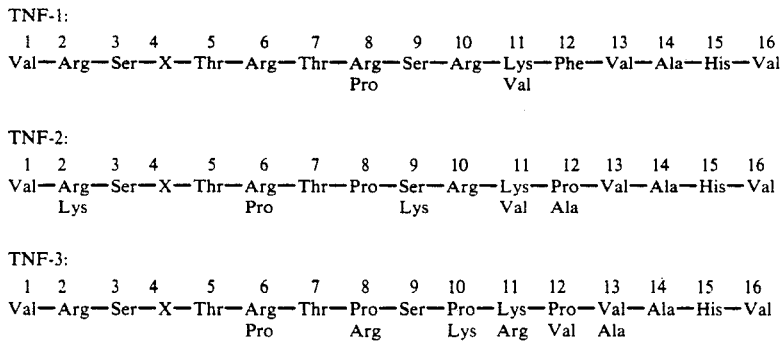

The fourth amino acid represented by X in the above N-terminal amino acid sequence is an amino acid which cannot be identified with any of the gas phase amino acid sequencer now available; it is certain that it is not Ser, and possibly it is Cys which is an amino acid not detectable by any prior art method.

Separately, 3.3 µg of trypsin was added to 100 µl of an aqueous solution containing 100 µg of the anti-tumor polypeptide (a mixture of TNF-1, TNF-2, and TNF-3) which showed a single band in SDS-PAGE, and the resulting mixture was allowed to stand at 37° C., at pH 8.0 for 20 hours for trypsin hydrolysis. The hydrolysates were separated as F-1 to F-8 fragments, respectively, by HPLC using RP318 column (a column for reverse phase manufactured by Biorad Corp.). The respective fragments were subjected to Edmon degradation with an amino acid sequencing analyzer manufactured by Applied Biosystems Inc. (Model 470A). The isolated phenylthiohydantoin was analyzed by HPLC (Shimazu Model LC-4A) to determine the amino acid sequence in a conventional manner. The results were as follows:

F-1: Val-Val-Ala-Asn-Pro-Gln-Ala-Glu-Gly-Gln-Leu-Gln
F-2: Ala-Asn-Ala-Leu-Leu-Ala
F-3: Asn-Gln-Leu-Val-Val-X-X-X-Gly-Leu
F-4: Ile-Ala-Val-X-Tyr
F-5: VAl-Asn-Leu-Leu
F-6: Glu-Thr-Pro-Glu-Gly-Ala-Glu-Ala
F-7: Tyr-Glu-Pro-Ile-Tyr-Leu-Gly-Gly-X-Phe
F-8: Leu-Ser-Ala-Glu-Ile-Asn-Arg-Pro-Asp-Tyr-Leu-Asp-Phe-Ala-Glu-Ser-Gly-Gln-Val-Tyr

(3) Preparation of a Synthetic Probe

Of the amino acid sequences of the above anti-tumor polypeptides, DNA corresponding to the eight amino acids of F-7 shown in TABLE 2 was synthesized in the solid phase method.

TABLE 2

| Amino acid sequence | Tyr | — | Glu | — | Pro | — | Ile | — | Tyr | — | Leu | — | Gly | — | Gly |
|---|---|---|---|---|---|---|---|---|---|---|---|---|---|---|---|
| Base sequence | TA<br>T<br>C | | GA<br>A<br>G | — | CCG<br>A<br>C<br>T | —ATC—<br>T | | | TA<br>T<br>C | — | TT<br>A<br>G<br>CTG<br>C<br>T | — | GGG<br>A<br>C<br>T | — | GG<br>C<br>T |

(4) Extraction of mRNAs from THP-1 Cells

THP-1 cells were cultured in a 10% FBS-containing RPM-1-1640 medium at 37° C. in the presence of 5% $CO_2$. When the number of cell reached $1 \times 10^6$/ml, 100 μg/ml of 12-tetradecanoylphorbol-13-acetate (hereunder referred to only as TPA) was added to the medium, and the culturing was continued. The cells collected 8 and 70 hours after addition of TPA were employed for extraction of mRNAs.

The extraction of the mRNAs from the cells was conducted as follows.

The cells were collected by centrifugation, and washed once with PBS (−) (0.8% NaCl+0.02% KCl+0.02% $KH_2PO_4$+0.115% $Na_2HPO_4$). The collected cells were well suspended in 50 ml of a buffer solution for extraction of RNAs followed by addition of Nonident-P40 to obtain a final concentration of 0.5% and treatment with a Teflon homogenizer at 10 strokes to crush the cells. Thereafter, the homogenate was subjected to centrifugation at 10000 g at 4° C. for 1 min. to obtain cell extracts in the supernatant. An equal volume of a buffer-saturated phenol/chloroform mixed solvent was added to the cell extracts, and the mixture was mixed at room temperature for over 30 min. followed by centrifugation at 3000 g for 10 min. to remove the phenol/chloroform solvent layer. The extraction with phenol/chloroform was conducted two more times.

Next, an equal volume of chloroform/isoamyl alcohol (24:1) was added to the supernatant followed by mixing at room temperature for 10 min. or more and centrifugation to recover the supernatant.

Ethanol in a volume of 2.5 times as much as the supernatant was added to the latter, and the mixture was allowed to stand at −20° C. overnight to precipitate the RNA which was then recovered by centrifugation at 10000 g at 4° C. for 10 minutes to obtain a cytoplasmic RNA sample. The precipitate was suspended in 20 ml of sterilized water, and a portion of the suspension was used to determine the RNA concentration. 5 Ml of an RNA-washing buffer solution at a concentration of five times that of the RNA suspension was added to the latter, and the resulting mixture was passed through a poly (U) Sepharose column reviously equilibrated with the RNA-washing buffer solution. After rRNA and tRNA other than poly (A) RNA were washed off, the latter was eluted with 5 ml of formamide. The poly (A) RNA fractions were collected, and then subjected to ethanol precipitation twice. The precipitate was suspended in sterilized water to obtain a poly (A) RNA concentration of 1 μg/μl, and then subdivided for storage at −80° C. Hereunder, poly (A) RNA is referred to as mRNA.

(5) Preparation of cDNA Library

A cDNA library was prepared in two ways using the mRNA obtained as in the above manner.

(1) Gubler Method ("Gene", 25, pp. 263–269, 1983)

In a conventional manner oligo (dT) complementary to the 3'-poly (A) sequence of mRNA was annealed with mRNA to prepare a primer for reverse transcriptase. Then, the primer was subjected to the reaction of the reverse transcriptase in the presence of dATP, dGTP, dCTP, and dTTP to synthesize a cDNA complementary to the mRNA. Thereafter, the thus-obtained mRNA/cDNA hybrid was nicked with RNaseH at the mRNA region and the mRNA was replaced by DNA polymerase 1 and *E. coli* DNA lygase to synthesize double-strand DNA. The 3'-end of the thus-obtained double-strand DNA was labeled with terminal deoxynucleotidyl transferase to add 10-20 dC tails thereto. Then, plasmid vector pBR322 replicable in *E. coli* was treated with restriction enzyme Pstl to prepare linear plasmid DNA. This was then labeled at the 3'-end with terminal deoxynucleotidyl transferase to add 10-20 dC tails thereto. Then, the dC-tailed plasmid vector and the dC-tailed double-strand DNA were annealed and then transferred to *E. coli* by transformation with calcium to provide the transformed strain as a cDNA library, (ii)Okayama-Barg Method ("Molecular and Cellular Biology", 2, pp. 161-170, 1980)

In contrast to the Gubler method, double-strand DNA with oligo (dT) tails complementary to the poly (A) sequence of mRNA was annealed and reacted with reverse transcriptase in the presence of dATP, dGTP, dCTP, and dTTP to synthesize the complementary cDNA. Next, this newly-synthesized cDNA was labeled with terminal deoxynucleotidyl transferase to add dC-tails thereto followed by annealing with the previously dC-tailed plasmid vector and ligation to prepare a plasmid containing mRNA/cDNA hybrid. Next, similarly to the Gubler method, this plasmid was treated with RNaseH, DNA polymerase I and E. coli DNA ligase to replace the mRNA by DNA. Thus, a plasmid containing double-strand cDNA was obtained, this plasmid was introduced into E. coli cells to prepare a cDNA library.

(6) Screening for the Desired cDNA

The cDNA library obtained in the above-described manner was grown on a nitrocellulose filter and then in a medium containing chloramphenicol ("Gene", 10, pp. 63-67, 1980) to increase the number of plasmids.

Then, the nitrocellulose filter on which the cDNA library had grown was immersed in a 0.5N NaOH solution to break the *E. coli* cell walls as well as to separate the double-strand of the plasmid DNA into two single-strands which were then immersed into a 1M Tris-HCl solution (pH 7.5) and allowed to stand at room temperature for 10 minutes. Next, the nitrocellulose filter was immersed into a 0.5M Tris-HCl (pH 7.5)/1.5M NaCl solution at room temperature for 10 minutes and then allowed to be air-dried, after being dried well, the nitrocellulose filter was treated at 80° C. for 2 hours. The 5'-end of the synthesized DNA harboring 23 bases was labeled with T$^{32}$PATP, T4DNA kinase, and this labeled 5'-end was used thereafter as the DNA probe in screening for cDNA clones. The nitrocellulose filter treated at 80° C. was hybridized in six volumes of NET (1×NET, 0.15M NaCl, 0.015M Tris-HCl at pH 7.5, 1 mM EDTA, 250 μg/ml of E. coli tRNA and 0.5% of NP-40) at 42° C. overnight and then washed with six volumes of SSC (1×SSC. 0.15M NaCl and 0.015M sodium citrate) at 0° C. The nitrocellulose filter was further washed twice with two volumes of SSC each time at 0° C. for 5 minutes and air-dried followed by autoradiography.

The clones found to be positive by autoradiography were subjected to the Maxam-Gilbert base sequencing method to determine their base sequences to narrow the positive clone candidates.

It was found that a cDNA clone having the C-end of the anti-tumor polypeptide was present in cDNA clones which hybridize with the synthetic DNA consisting of 23 bases. This cDNA clone was found to have about 1000 base pairs.

(7) Preparation of Genome DNA

THP-1 cells (3×10$^9$) were cultured in a medium containing 100 ng/ml of TPA for 8 hours and then suspended in 100 ml of 150 mM NaCl+100 mM EDTA solution followed by addition of 10 ml of 10M sodium perchlorate and 10 ml of 10% SDS. Next, 12 ml of 5M NaCl were added to the mixture followed by warming at 60° C. for 15 minutes. An equal volume of a chloroform-isoamyl alcohol (24:1) mixture was added to the resulting solution which was then mixed gently. The mixture was placed in a Hitachi quick-freezing centrifuge for centrifugation at 10,000 r.p.m. for 10 minutes to obtain a supernatant. An equal volume of isopropyl alcohol was added to the supernatant, and the resulting DNA precipitate was rolled around a Pasteur pipette. The DNA was washed with 70% ethanol and then dissolved in 100 ml of a 10 mM Tris-HCl (pH 7.5)+10 mM NaCl+0.1 mM EDTA solution (TSE). Next, 10% SDS was added to the solution to a final concentration of 0.5% followed by addition of protease K to a final concentration of 1 mg/ml and warming at 55° C. was performed overnight. Here, separately, DNA-protein complex in the intermediate layer produced by the above centrifugation at 10,000 r.p.m. was separated and subjected to the same procedures as mentioned above after the centrifugation to obtain an additional yield of the DNA.

The DNA solution treated with the protease was gently mixed with a water-saturated phenol+m-cresol+isoamyl alcohol (100:14:0.1) mixture and then subjected to centrifugation at 300 r.p.m. at normal temperature for 10 minutes to separate the supernatant. An equal volume of isopropanol was added to the supernatant, and the resulting precipitate was rolled around a Pasteur pipette. The DNA was washed with 70% ethanol and dissolved in 100 ml of TSE.

TSE was added to the DNA solution to a final concentration of 800 μg/ml followed by addition of 0.95 g/ml of CsCl and further of one tenth volume of an ethidium bromide solution (5 mg/ml) to produce a homogenous solution which was then subjected to centrifugation with a Beckman type-60 rotor at 45000 r.p.m. at 20° C. for 48 hours for purification of the DNA by the density-gradient method. After the centrifugation was completed, the DNA was recovered with a Pasteur pipette while pursuing the DNA band by irradiation of UV at 360 nm. Next, CsCl-saturated isopropyl alcohol was added to the DNA solution and mixed therewith several times. This mixing was repeated ten times to remove the ethidium bromide.

The thus-prepared DNA solution was dialyzed against 2 l of TSE at 4° C. for twenty-four hours to obtain the DNA. The DNA concentration was 650 μg/ml and 18 mg of the DNA was obtained.

(8) Recovery of Genome DNA Fragments

The DNA obtained in the manner described above was subdivided into 15 μg portions, and subjected to the action of several kinds of restriction enzymes for its complete decomposition. The lengths of the anti-tumor polypeptide gene fragments obtained by the action of the enzymes were analyzed by the Southern method. Namely, 50 units each of ApaI (GGGCCC), XhoI (CTCGAG), BamHI (GGATCC), EcoRI (GAATTC), SstI (GAGCTC) and KpnI (GCTACC) were employed, and the DAN was warmed in an appropriately-buffered solution having an appropriate saline concentration at 37° C. overnight. At the end of the reaction, 5M NaCl was added to the reaction mixture to a final concentration of 0.25M followed by addition of 2.5 volumes of ethanol to precipitate the DNA. The DNA decomposition products were recovered as precipitates by centrifugation and dissolved in 10 μl of water which was then developed on 1.5% agar gel. Next, the DNA fragments were adsorbed on a nitrocellulose filter. The nitrocellulose filter with the DNA adsorbed thereon was air-dried and then treated under vacuum at 80° C. for 2 hours Nick Translation Two hundred ng of the cDNA obtained in the above-described screening step (6) were dissolved in 30 μl of a reaction solution [50 mM Tris-HCl (pH 7.5)+10 mM MgCl$_2$+10 mM DTT] and 20 μC of α-$^{32}$PdCTP and 5 μM each of dATP, dGTP, and dTTP were added to the resulting solution followed by addition of 12.5 pg of DNase and 10 units of DNA polymerase. Reaction was carried out at 20° C. for one hour. After the reaction was completed, an equal volume of a water-saturated phenol-chloroform (1:1) mixture was added to the reaction mixture which was then stirred vigorously and subjected to centrifugation for protein removal. Furthermore, an equal volume of chloroform was added to the solution followed by vigorous stirring and centrifugation to separate the aqueous layer. This aqueous layer was put into a Sephadex G-50 column previously equilibrated with a solution containing 1 mM EDTA and 100 μg/ml of tRNA, and elution was conducted with a solution containing 1 mM EDTA and 100 μg/ml of tRNA to recover DNA fractions. The thus-obtained labeled DNA had a radioactivity of 1×10$^8$ cpm/μg DNA. This DNA was warmed at 100° C. for 10 minutes to form single-strand DNA for use as the probe.

Hybridization

The nitrocellulose filter with the DNA adsorbed thereon was uniformly immersed into 1 ml of a solution containing 50% formaldehyde, 5×SSC (0.15M NaCl+0.015 sodium citrate), 5×FBP, 1% glycine, a 20 mM phosphate buffer solution (pH 6.8) and 100 μg/ml of calf thymus degenerated DNA, and was then sealed in a plastic bag followed by warming at 42° C. overnight. The filter was immersed into 1 ml of a solution containing 50% formaldehyde, 5×SSC, 1×FBP, a 20 mM phosphate butter solution (pH 6.8), and 100 μg/ml of calf thymus degenerated DNA with $2 \times 10^7$ c.p.m. of the probe added thereto and warmed at 42° C. overnight. At the end of the warming, the nitrocellulose filter was transferred to a 2×SSC solution for one hour washing at 68° C. to prevent adsorption of non-specific DNA probes. The washing was repeated with 0.1×SSC for 5 minutes, and the filter was air-dried. DNA fragments which specifically hybridize with the probe were detected by exposure of Kodak X-ray film for twenty-four hours.

Concentration of Specific DNA Fragment

In the above-described Southern hybridzation, the probe DNA mentioned in step (6) and the 2.6 kb DNA fragment produced when the cleavage of the genome DNA was conducted using restriction enzyme ApaI showed very-reproducible hybridization. Thus 1500 units of ApaI were added to 5 ml of a reaction solution containing 1.3 mg of genome DNA of THP-1, and the mixture was warmed overnight to obtain complete cleavage products of the genome DNA of THP-1 by ApaI.

The resulting DNA fragments were partioned by 1.5% agar gel, and an agar gel portion of around 2.6 kb was cut off. Recovery of the DNA from the agar was conducted as follows.

First, the agar was added to 15 ml of a solution prepared by adding 22.5 g of KI to 15 ml of a 10 mM phosphate butter solution (pH 7.0), and the mixture was warmed to 60° C. to dissolve the agar. Thereafter, the DNA-containing solution was adsorbed on "Biogel HTP" manufactured by Biorad Corp., washed well with a 10 mM phosphate butter solution, and then the DNA was eluted with a 1M phosphate butter solution and 0.5% SDS followed by dialysis against TSE at 4° C. for twenty four hours.

(9) Preparation of Genome Library

Terminal deoxynucleotidyl transferase was used to add dCTP tails to the obtained DNA, Separately, pNF used as the vector was made into single strands with KpnI and tailed with dCTP. The two tailed ones were annealed with each other to form a cyclic chimera. This chimera was incorporated into *E. coli* RRI to prepare a library comprising $2 \times 10^4$ independent colonies.

Figure 3:
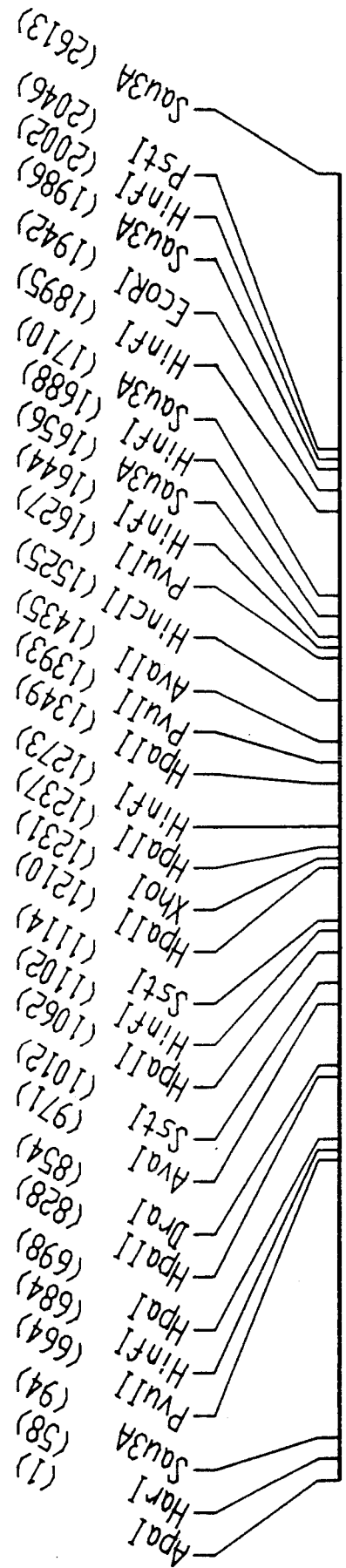
FIG. 3 shows a restriction enzyme map of the genome gene of the above anti-tumor polypeptide.

The above-mentioned probe was employed to choose the above genome library, thereby providing a clone. The restriction enzyme map of the obtained clone and its partial base sequece are shown in FIGS. 3 and 4, respectively.

(10) Expression of the Genome Gene in *E. coli*

The restriction enzyme XhoI/PstI fragment of the genome gene obtained in step (1) above (811 base DNA fragment of from the 340th to 1150th bases of the partial base sequence of the TNF genome DNA mentioned above) was inserted into plasmid vector pUC12 (manufactured by Pharmacia AB) at its restriction enzyme SalI/PstI site to form plasmid pUC12$^{TNF}$x/p. This plasmid has the promotor region, operator region and SD sequence of lactose operon region, and further possesses, downstream of those regions, a synkaryon gene consisting of 45 bp involving the 5'-terminal region of a β-galactosidase gene and the genome gene attached thereto. Thus, the protein expressed by *E. coli* incorporating this plasmid therein is a composite protein comprising the base sequence of the N-terminal region of β-galactosidase and the genome DNA fragment (FIG. 5).

(II) The 811 bp restriction enzyme XhoI/PstI fragment of the genome was inserted into plasmid vector pUC540 having a Tac promoter and an SD sequence at the restriction enzyme SalI/PstI site to prepare plasmid pUC540$^{TNF}$x/p.

This plasmid has a gene coding a protein which has the first methionine present in the restriction enzyme XhoI/PstI fragment of the genome gene at its N-end (FIG. 6).

Plasmid vector pUC540 is prepared by cloning the EcoI/BamHI fragment of plasmid pDR540 which has a Tac promotor (commercially available from Pharmacia AB) to the EcoRI/BamHI site of plasmid vector pUC8 (commercially available from the same company).

(III) Plasmid pUC540$^{TNF}$x/p has a restriction enzyme BamHI site downstream of the SD sequence. So, if an exogenous gene is inserted at this BamHI site, its expression is made possible only by addition of isopropyl β-D-thiogalactopyranoside (hereunder referred to as IPTG).

Therefore, *E. coli* JM 103 incorporating the above plasmid p12$^{TNF}$x/p or pUC540$^{TNF}$x/p therein was precultured in a 1×YT medium containing 50 μg/ml of ampicillin (0.8% bactotrypton+0.5% bactoyeasts+0.5% NaCl) at 37° C., and then transferred in a proportion of 1% to a 500 ml Sakaguchi flask containing 100 ml of 1×YT medium with 50 μg/ml of ampicillin incorporated therein followed by culturing at 37° C. in the same manner as described above. When the OD$_{660}$ reached 0.3, IPTG was added to the mixture to a final concentration of 2 mM, and then the culturing was continued. The thus-treated *E. coli* cells were collected with a centrifuge, washed with 1× PBS (0.8% NaCl+0.02% KCl+0.02% KH$_2$PO$_4$+0.115% Na$_2$HPO$_4$), and suspended in 10 ml of 1×PBS again. Ultrasonic waves were applied to the suspension to crush the *E. coli* cells. Part of the crushed cells were used to determine the anti-tumor activity. This determination was carried out by a sensitivity test using L-929 cells as the indicator. The results are shown in Table 3.

TABLE 3

| Plasmid | TNF activity (units/ml) |
|---|---|
| p12$^{TNF}$x/p | 15 |
| pUC540$^{TNF}$x/p | 19 |
| pUC12/JM103 | Not detected. |

EXAMPLE 2

Plasmid pUC540$^{TNF}$x/p has the restriction enzyme BamHI site downstream of the SD sequence. Accordingly, if an exogenous gene is inserted at this BamHI site, the gene can be expressed only by addition of IPTG thereto.

Figure 7:
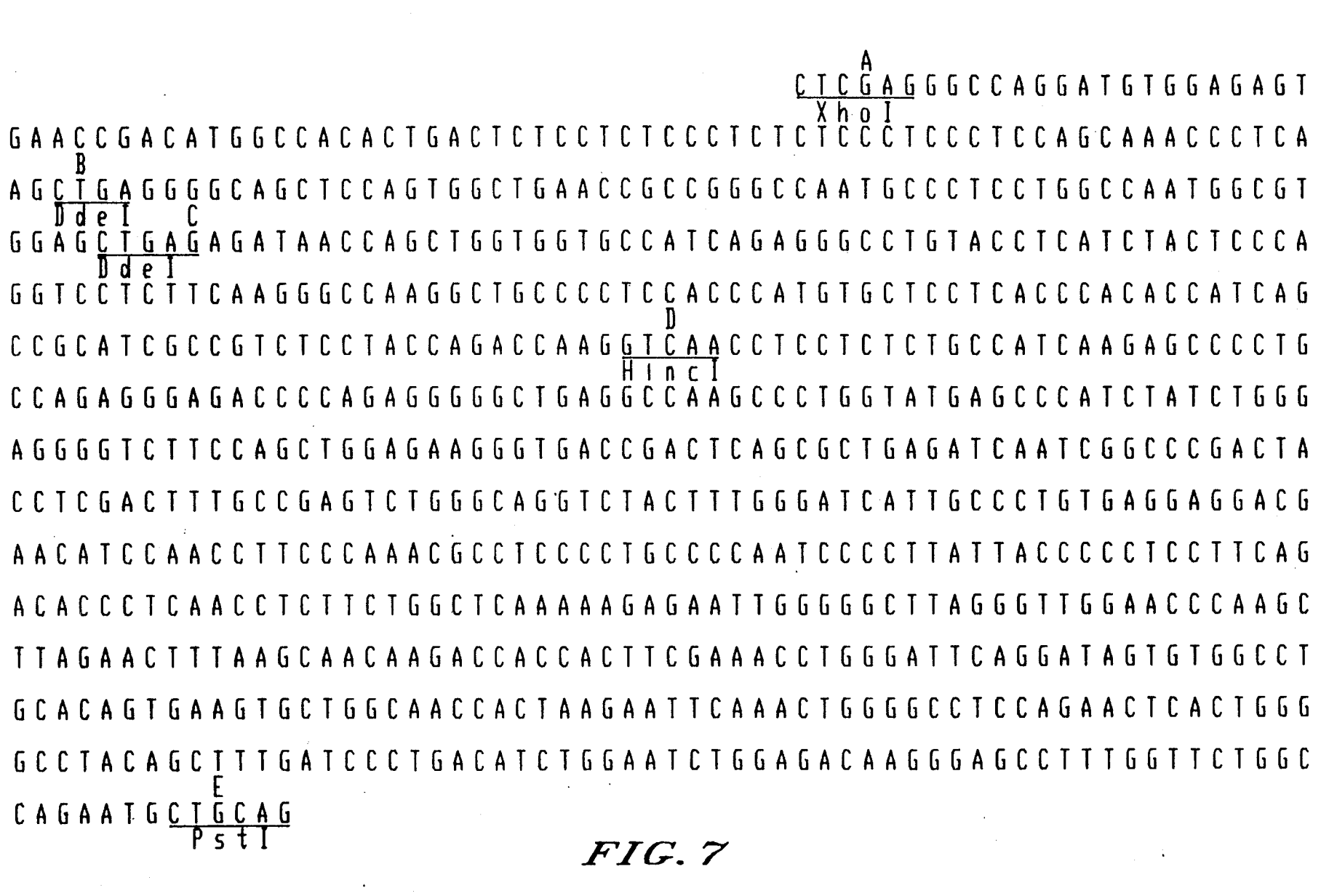

The genome gene shown in FIG. 3 was cleaved with XhoI and PstI, and the XhoI/PstI fragment shown in FIG. 7 was recovered. Then, this fragment was cleaved with HincII fragment to recover 294 bp XHoI-HincII fragment and 521 bp HincII/PstI fragment. The 294 bp fragment was partially cleaved with DdeI to recover 206 bp DdeI/HincII fragment. The thus-recovered 521 bp HincII/PstI fragment and 206 bp DdeI/HincII fragment were combined with 69/70 bp, 72/73 bp or 21/22 bp double-strand DNA, respectively, and then inserted into pUC540$^{TNF}$x/p at its BamHI/PstI site. All the thus-obtained three plasmids pUC540$^{TNF}$69/70, pUC540$^{TNF}$72/73, and pUC540$^{TNF}$21/22 are under control of the promotor of lactose operon, and thus these three synthesized genes can be expressed in *E. coli*.

and their expression was investigated by addition of IPTG. The induction time with IPTG was set to 12 hours. The results are shown in Table 5.

TABLE 5

| Plasmid | Anti-tumor activity (Units/50 ml) |
|---|---|
| pUC540$^{TNF}$72/73 | $3 \times 10^6$ |
| pUC540$^{TNF}$69/70 | $3 \times 10^4$ |
| pUC540$^{TNF}$21/22 | $3 \times 10^5$ |

EXAMPLE 3

In the same manner as in Example 2, 521 bp HincII/PstI fragment and 206 bp DdeI/HineII fragment were combined with 72/73 bp double-strand DNA shown in Table 6, and then inserted into pUC540$^{TNF}$X/P at its BamHI/PstI site.

TABLE 4

Base sequence of synthetic DNA

69/70 bp

Met Val Ser Ser Ser Arg Thr Pro Ser Asp Lys Pro Val Ala

5'-GATCCATGGTCAGCTCTTCTCGAACCCCGAGTGACAAGCCTGTAGCC
   GTACCAGTCGAGAAGAGCTTGGGGCTCACTGTTCGGACATCGG

His Val Val Ala Asn Pro Gln

CATGTTGTAGCAAACCCTCAAGC
GTACAACATCGTTTGGGAGTTCGACT

72/73 bp

Met Val Arg Ser Ser Ser Arg Thr Pro Ser Asp Lys Pro Val

GATCCATGGTACGTAGCTCTTCTCGAACCCCGAGTGACAAGCCTGTA
GTACCATGCATCGAGAAGAGCTTGGGGCTCACTGTTCGGACAT

Ala His Val Val Ala Asn Pro Gln

GCCCATGTTGTAGCAAACCCTCAAGC
CGGGTACAACATCGTTTGGGAGTTCGACT

21/22 bp

Met Ala Asn Pro Gln

GATCCATGGCAAACCCTCAAGC
GTACCGTTTGGGAGTTCGACT

Each of the above three plasmids was incorporated into *E. coli* JM103 in the same manner as in Example 1,

TABLE 6

Base sequence of synthetic DNA

72/73 bp

Met Val Lys Ser Cys Thr Arg Thr Pro Ser Arg Lys Pro Val

5'-GATCCATGGTCAAATCTTGCACCCGAACCCCTTCACGGAAGCCTGTA
   GTACCAGTTTAGAACGTGGGCTTGGGGAAGTGCCTTCGGACAT

Ala His Val Val Ala Asn Pro Gln

GCCCATGTTGTCGCGAACCCTCAAGC
CGGGTACAACAGCGCTTGGGAGTTCGACT

Other 32 type 72/73 bp

Met Val Arg Ser Cys Thr Arg Thr Pro Ser Arg Lys Pro Val

5'-GATCCATGGTTAGAAGCTGCACCCGTACCCCGAGCCGTAAACCGGTA
   GTACCAATCTTCGACGTGGGCATGGGGCTCGGCATTTGGCCAT

TABLE 6-continued

Base sequence of synthetic DNA

```
         or          or          or                      or          or
         Lys         Ser         Pro                     Pro         Ala
         ┌─┐         ┌─┐         ┌─┐                     ┌─┐         ┌─┐
         AAA         TCC         CCT                     CCT         GCG
         TTT         AGG         GGA                     GGA         CGC
    Ala  His   Val   Val   Ala   Asn   Pro   Gln
    ┌─┐ ┌─┐   ┌─┐   ┌─┐   ┌─┐   ┌─┐   ┌─┐   ┌─┐
    GCC CAT   GTT   GTA   GCG   AAC   CCT   CAAGC
    CGG GTA   CAA   CAT   CGC   TTG   GGA   GTTCGACT
```

(IV) Each of the thus-prepared recombinant TNFs are combined with the BamHI downstream region of a Tac promotor, and has the initiation codon ATG immediately after the restriction enzyme BamHI cleavage point, the first codon of the second amino acid which follows the ATG being G.

All the thus-constructed genes are controlled by the promotor of the lactose operon, and their expression is inductive with IPTG.

Cytoxic Effects on L-929 Cells

*E. coli* JM103 with pUC540AMCT-1 incorporated therein (deposited with the Fermentation Research Institute (FRI) in Japan as No. 8630 since Jan. 31, 1986), which corresponds to one of the DNAs of the present invention where X is a hydrogen atom, and X' is Met-Val-Lys-Ser-Cys-Thr-Arg-Thr-Pro-Ser-Arg-Lys-Pro-Val-Ala-His-Val-Val, was pre-cultured in a 1×YT medium containing 50 μg/ml of ampicillin (0.8% bactotrypton+0.5% bactoyeast extracts+0.5% NaCl) at 37° C., and then transferred in a proportion of 1% to a 500 ml of a Sakaguchi flask containing 100 ml of a 1×YT medium with 50 μg/ml of ampicillin added thereto. The mixture was cultured in the same manner at 37° C. When the $OD_{660}$ reached 0.3, IPTG was added to the culture to a final concentration of 0.7 mM followed by further culturing for twenty-four hours. The thus-obtained *E. coli* was collected with a centrifuge, washed with 1×PBS (0.8% NaCl+0.02% KCl+0.02% $KH_2PO_4$+0.115% $Na_2HPO_4$), and suspended in 10 ml of 1×PBS, followed by application of ultrasonic waves to the culture to crush the *E. coli* cells. Part of the thus-treated cells were used to determine the anti-tumor activity. The results of sensitivity tests using L-929 cells as the indicator are shown in Table 7.

TABLE 7

| Plasmid | TNF activity (units/ml) |
| --- | --- |
| pUC540AMCT-1 | 80,000 |

Cytotoxic Effects on T-24 Cells (1) 1×10⁴/well of T-24 cells were suspended in a mixture of RPMI1640 and 10 w/w % FCS, and then grown in a Linbro 96-well microtiter plate followed by culturing at 37° C. for 48 hours in the presence of 0.5% of $CO_2$. Thereafter, pUC540AMCT-1 was added to the culture in a quantity of 5250 units/ml and 525 units/ml, and the culturing was continued for an additional twenty-four hours. Next, the anti-tumor effects were determined by the Crystal Violet staining method. The results are shown in Table 8.

TABLE 8

| Quantity (units/ml) | T-24 cell survival (%) |
| --- | --- |
| 5250 | 0 |
| 525 | 0 |

In the same manner, the cytotoxicity to T-24 cells of a polypeptide represented by Met-Val-Arg-Ser-Ser-Ser-Arg-Thr-Pro-Ser-Asp-Lys-Pro-Val-Ala-His-Val-Val- or Met-Lys-Pro-Val-Ala-His-Val-Val-Ala-Asn-Pro-Gln-Ala-Glu-Gly-Gln-Leu-Gln-Trp-Leu-Asn-Arg-Arg-Ala-Asn-Ala-Leu-Leu-Ala-Asn-Gly-Val-Glu-Leu-Arg-Asp-Asn-Gln-Leu-Val-Val-Pro-Ser-Glu-Gly-Leu-Tyr-Leu-Ile-Tyr-Ser-Gln-Val-Leu-Phe-Lys-Gly-Gln-Gly-Cys-Pro-Ser-Thr-His-Val-Leu-Leu-Thr-His-Thr-Ile-Ser-Arg-Ile-Ala-Val-Ser-Tyr-Gln-Thr-Lys-Val-Asn-Leu-Leu-Ser-Ala-Ile-Lys-Ser-Pro-Cys-Gln-Arg-Glu-Thr-Pro-Glu-Gly-Ala-Glu-Ala-Lys-Pro-Trp-Tyr-Glu-Pro-Ile-Tyr-Leu-Gly-Gly-Val-Phe-Gln-Leu-Glu-Lys-Gly-Asp-Arg-Leu-Ser-Ala-Glu-Ile-Asn-Arg-Pro-Asp-Tyr-Leu-Asp-Phe-Ala-Glu-Ser-Gly-Gln-Val-Tyr-Phe-Gly-Ile-Ile-Ala-Leu was determined (the proportions of the net basic amino acid residue as defined above are about 11.8%, and 14.3%, respectively, and other corresponding polypeptides having lower values were found to be of no significance even at as high a dose as 5000 units/ml).

(2) 1×10⁴/well of T-24 cells were suspended in a mixture of RPMI1640 and 10 w/w % FCS, and then grown in a Linbro 96-well microtiter plate followed by culturing at 37° C. for 48 hours in the presence of 0.5% $CO_2$. Thereafter, pUC540AMCT-1 was added to the culture in a quantity of 18.7 units/ml, 62.5 units/ml, 187.5 units/ml, 625 units/ml and 1875 units/ml, respectively, and the culture was continued for an additional twenty-four hours. Next, 1 μCl/ml of ³H-thymidine was added to the culture followed by culturing for an additional nine hours. The ³H-thymidine taken in by the cells counted with a liquid scintillation counter to determine the suppression effect on the ³H-thymidine intake in order to evaluate the anti-tumor effects. The results are shown in Table 9.

TABLE 9

| pUC540AMCT-1 (units/ml) | Suppression rate in ³H-thymidine taken in by T-24 cells (%) |
| --- | --- |
| 18.7 | 9 |
| 62.5 | 28 |
| 187.5 | 41 |
| 625 | 69 |
| 1875 | 81 |

EXAMPLE 4

Each of pUC540$^{TNF}$21/22, pUC540$^{TNF}$69/70 and pUC540$^{TNF}$72/73 prepared in Example 2 is a recombinant TNF which is combined with the BamHI downstream region of a Tac promotor, and which has the initiation codon ATG immediately after the restriction enzyme BamHI cleavage point, the first codon of the second amino acid which follows the ATG being G.

50 μg each of these recombinants were completely cleaved with 50 units of restriction enzyme NcoI (Japan Gene Corp.). After the complete cleavage was confirmed, the mixture was passed through a Sephadex G-50 column to purify the DNAs. Next, a 1 μg portion of each of the DNAs was converted to complete double-strand DNA by repair at the NcoI cleavage point with a DNA polymerase Klenow fragment, and the ligation was conducted using

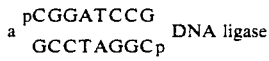

consisting of 8 bp to prepare cyclic double-strand DNAs which were named pUC540$^{TNF}$Nco21/22, pUC540$^{TNF}$Nco69/70, and pUC540$^{TNF}$Nco72/73, respectively.

All the thus-constructed genes are controlled by the promotor of the lactose operon, and their expression is inductive with IPTG.

Cytotoxic Effects of L-929 Cells

E. coli JM103 with pUC540$^{TNF}$Nco21/22, 69/70 or 72/73 incorporated therein (deposited with the Fermentation Research Institute (FRI) in Japan as Nos. 8628, 8629, and 8627, respectively, since Jan. 31, 1986) was pre-cultured in a 1×YT medium containing 50 μg/ml of ampicillin (0.8% bactotrypton+0.5% bactoyeast extracts+0.5% NaCl) at 37° C., and then transferred in a proportion of 1% to a 500 ml of a Sakaguchi flask containing 100 ml of a 1×YT medium with 50 μg/ml of ampicillin added thereto. The mixture was cultured in the same manner at 37° C. When the OD$_{660}$ reached 0.3, IPTG was added to the culture to a final concentration of 0.7 mM followed by further culturing for twenty-four hours. The thus-obtained E. coli was collected with a centrifuge, washed with 1×PBS (0.8% NaCl+0.02% KCl+0.02% KH$_2$PO$_4$+0.115% Na$_2$HPO$_4$), and suspended in 10 ml of 1×PBS, followed by application of ultrasonic waves to the culture to crush the E. coli cells. Part of the thus-treated cells were used to determine the anti-tumor activity. The results of sensitivity tests using L-929 cells as the indicator are shown in Table 10.

TABLE 10

| Plasmid | TNF activity (units/ml) |
| --- | --- |
| pUC540$^{TNF}$Nco21/22 | 6250 |
| pUC540$^{TNF}$Nco69/70 | 6250 |
| pUC540$^{TNF}$Nco72/73 | 6250 |

Cytotoxic Effects on T-24 Cells

1×10$^4$/well of T-24 cells were suspended in a mixture of RPMI1640 and 10 w/w % FCS, and then grown in a Linbro 96-well microtiter plate followed by culturing at 37° C. for 48 hours in the presence of 0.5% CO$_2$. Thereafter, pUC540$^{TNF}$Nco21/22 was added to the culture in a quantity of 62.5 units/ml, 625 units/ml, and 1250 units/ml, and the culturing was continued for an additional twenty-four hours. Next, 1 μCl/ml of $^3$H-thymidine was added to the culture followed by nine more hours of culturing. The $^3$H-thymidine taken in by the cells counted with a liquid scintillation counter to determine the suppression effect on the $^3$H-thymidine intake in order to evaluate the anti-tumor effects. The results are shown in Table 11.

TABLE 11

| Quantity (units/ml) | $^3$H-thymidine (%)* |
| --- | --- |
| 62.5 | 54.3 |
| 625 | 25.6 |
| 1250 | 27.8 |

*represents the proportion (%) of the quantity of $^3$H-thymidine taken in to that in th case of no treatment with pUC540$^{TNF}$Nco21/22.

Cytotoxicity on WiDr (Colon Carcinoma)

Figure 8:
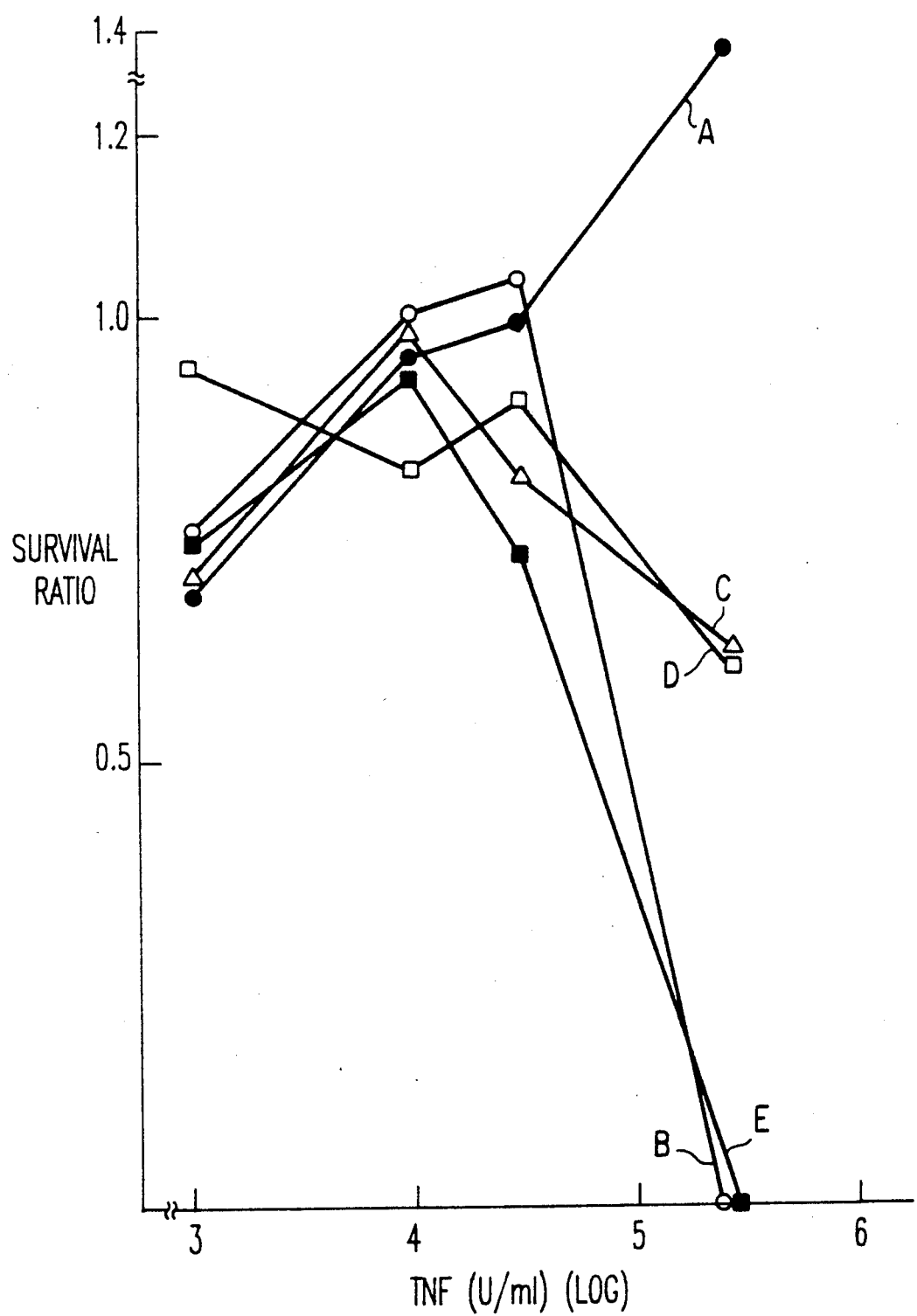
FIG. 8 is a graph exhibiting in vitro anti-tumor activity of some of the polypeptides of the present invention as compared with the prior art TNF.

Substantially in the same manner as for cytotoxicity on L-929 cells, cytotoxicity of some of the anti-tumor active polypeptides of the present invention on WiDr cells was studied. 4×10$^3$/well of WiDr cells were used, and the incubation time with the polypeptides was 48 hours. Each of the polypeptides was added in proportions of 10$^3$, 10$^4$, 5×10$^4$ and 3×10$^5$ units/ml. The results are shown in FIG. 8 wherein the symbols stands for:

A: the prior art TNF of Genentech Inc.
B: pUC540$^{TNF}$Nco72/73 (recombinant TNF of the present invention)
C: pUC540AMCT-1 (recombinant TNF of the present invention)
D: recombinant TNF of the present invention where X is a hydrogen atom, and X' is Met-Val-Arg-Ser-Cys-Thr-Pro-Thr-Pro-Ser-Arg-Lys-Pro-Val-Ala-His-Val-Val.
E: recombinant TNF of the present invention where X is a hydrogen atom, and X' is Met-Val-Lys-Ser-Ser-Thr-Arg-Thr-Pro-Ser-Arg-Lys-Pro-Val-Ala-His-Val-Val.

Comparisn of pUC540$^{TNF}$Nco72/73 of the Present Invention (TNF-5) with the Prior Art TNF of Genetech Inc. (TNF-G) in Cytotoxicity to Carcinoma Both were purified to a purity of 99% by affinity chromatography and confirmed to be sigle substances by electrophoresis.

In Vitro Activity Against T-24, A549 (Lung Carcinoma), LS174T (Colon Carcinoma) and WiDr The procedures used were substantially the same as in the case of L-929 cells. 1.0×10$^4$/well (4.0×10$^4$/well only in the case of T-24) were used, and the respective TNFs were added to the assay well in a proportion of 4% of the 8 μl final volume. The incubation was conducted at 37° C. in the presence of CO$_2$. 0.2% of crystal violet was used for staining, and the staining degree was measured on the basis of adsorption at OD$_{595}$ to calculate the survival ratios. The results in terms of ED$_{58}$ were as follows:

| Carcinoma | TNF-G (units/ml) | TNF-S (units/ml) |
| --- | --- | --- |
| T-24 | 10$^4$< | 10$^4$ |
| A549 | " | 5 × 10$^3$ |
| LS174T | " | 2.2 × 10$^3$ |
| WiDr | " | 1.5 × 10$^3$ |

In Vivo Activity Against B-16 Melanoma, MH134 Hepatoma and A549

(1) Four 8-week old C57BL/b mice were used for the respective TNFs purified with an immuno-column. LPS was used as the control. They were administered it according to the following schedule to evaluate the activity against B-16 melanoma.

| Days after inoculation of 3 × 10⁵ cells/id | TNF-G/head units | LPS | TNF-S/head units | LPS |
|---|---|---|---|---|
| 12 | 600 | 317 pg | 275 | 25 pg |
| 14 | 600 | 317 pg | 275 | 25 pg |
| 16 | 500 | 1.9 ng | 500 | 125 pg |
| 18 | 500 | 1.9 ng | 500 | 125 pg |
| 20 | 270 | 1.0 ng | 270 | 146 pg |

Figure 9:
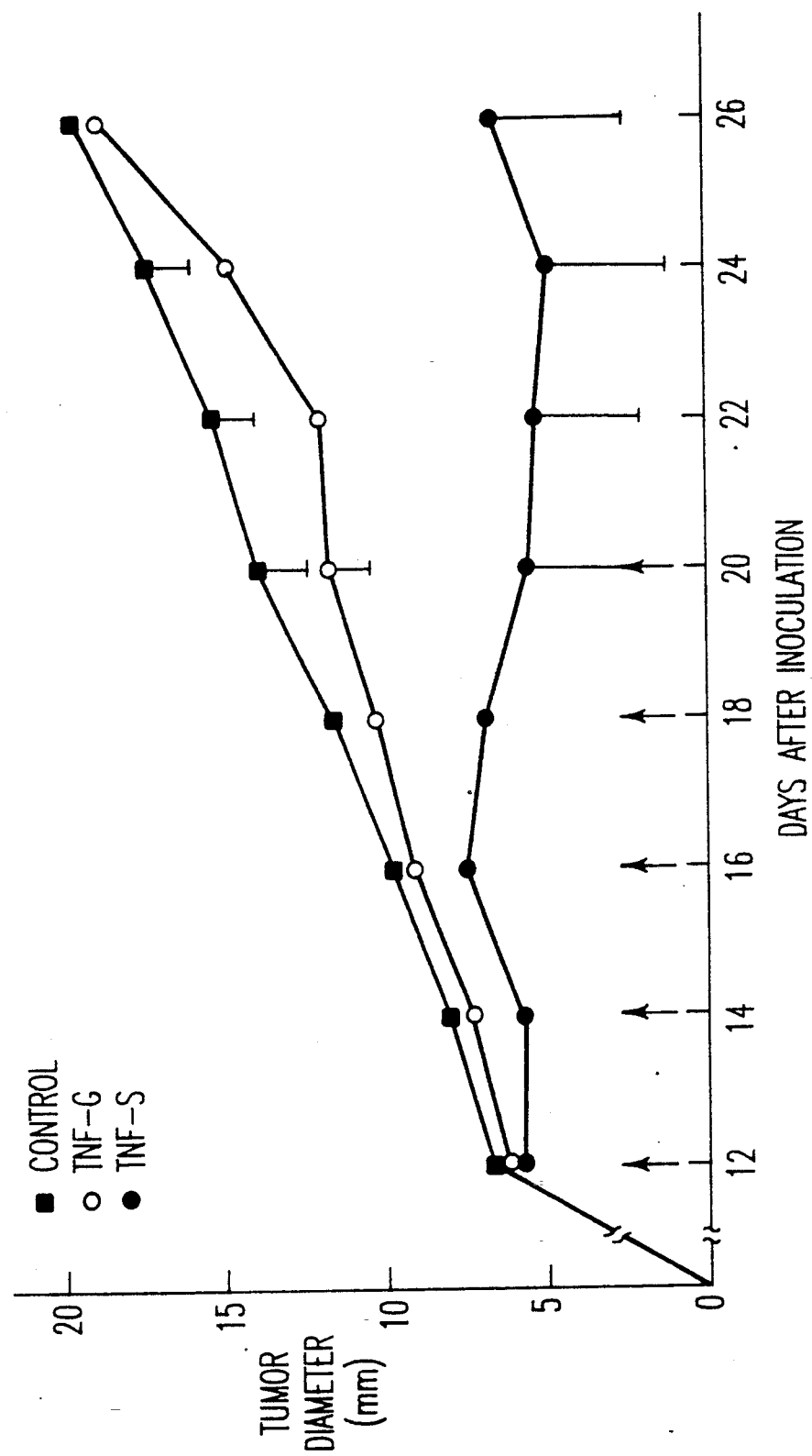
FIGS. 9-11 are graphs exhibiting in vivo anti-tumor activity of one of the polypeptides of the present invention as compared with the prior art TNF.

The results are shown in FIG. 9.

(2) Ten 8-week old C3H/HE mice were used for the respective TNFs purified with an immuno-column. LPS was used as the control. They were administered it according to the following schedule to evaluate the activity against MH134 Hepatoma:

| Days after inoculation of 2 × 10⁵ cells/id | TNF-G/head units | LPS | TNF-S/head units | LPS |
|---|---|---|---|---|
| 6 | 180 | 95 pg | 80 | 9.5 pg |
| 8 | 180 | 95 pg | 80 | 9.5 pg |
| 10 | 200 | 740 pg | 200 | 50 pg |
| 12 | 200 | 740 pg | 200 | 50 pg |
| 14 | 120 | 444 pg | 120 | 31 pg |

Figure 10:
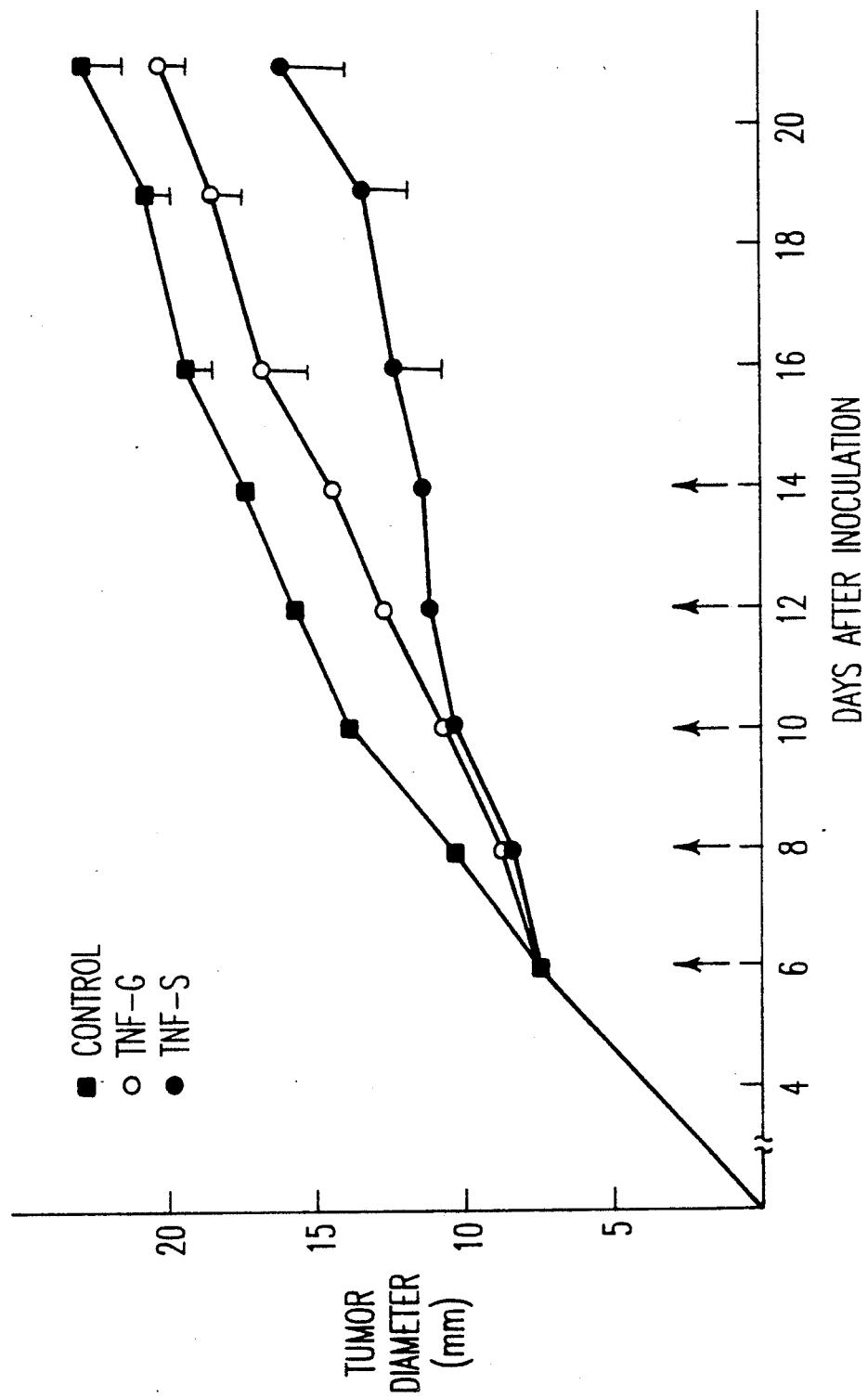

The results are shown in FIG. 10.

(3) Three 8 week old BALB/C-nuSlc mice were used for the respective TNFs purified with an immuno-column. LPS was used as the control. They were administered it according to the following schedule to evaluate the activity against A549.

| Days after inoculation of 5 × 10⁶ cells/id | TNF-G/head units | LPS | TNF-S/head units | LPS |
|---|---|---|---|---|
| 11 | 650 | 313 pg | 650 | 500 pg |
| 12 | 650 | 313 pg | 650 | 500 pg |
| 13 | 650 | 313 pg | 650 | 500 pg |
| 14 | 650 | 313 pg | 650 | 500 pg |
| 15 | 650 | 313 pg | 650 | 500 pg |

Figure 11:
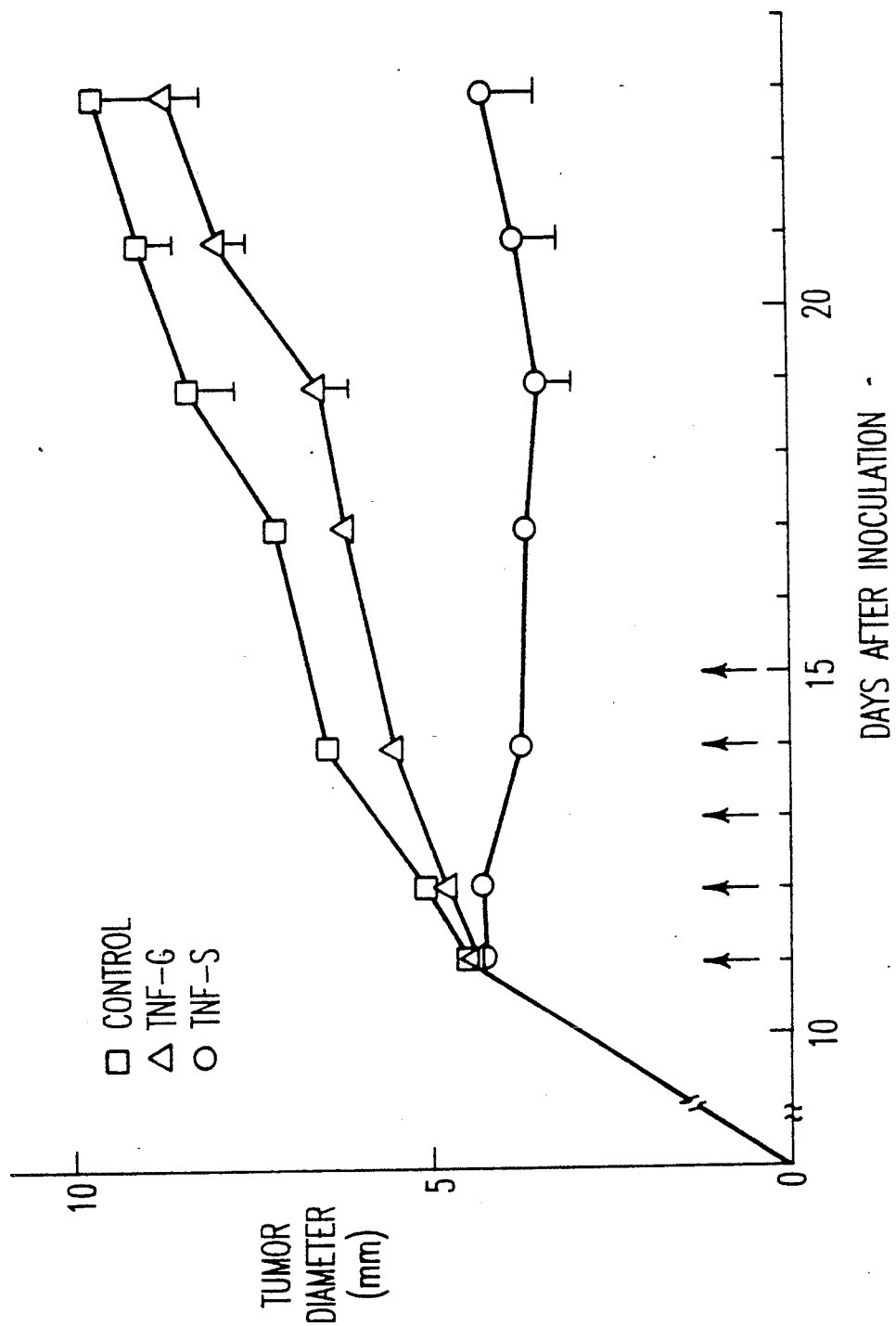

The results are shown in FIG. 11.

Synergistic Effects Attributable to Use in Combination

The following experiments were carried out to confirm synergistic anti-tumor activity in the case where the anti-tumor polypeptides with the X attached thereto of the present invention are used in combination with other polypeptides.

Each of the crushed E. coli cells containing the respective polypeptides prepared in the manner of the above-described examples was mixed in a volumetric ratio of 1:1, and the TNF activity was determined in a manner similar to that described in Example 1. The polypeptides used are listed below.

A:pUC540$^{TNF}$Nco72/73 (polypeptide without X attached thereto)
B:pUC540$^{TNF}$Nco21/22
C:pUC540$^{TNF}$Nco69/70
D:pUC540$^{TNF}$Nco72/73

(B, C and D are the X-attached polypeptides)

The results are shown in FIG. 12. The left graph in FIG. 12 is given as a reference only for the cases of individual use of the respective polypeptides.

As was mentioned in the above, the novel DNAs synthesized according to the present invention can express the novel anti-tumor polypeptides which are cytotoxic to human tumor cells, but not to normal cells. Furthermore, the present polypeptides are very cytotoxic even to T-24 cells to which the prior art TNF is reported to be entirely insensitive. The present invention provides also those polypeptides which are remarkably cytotoxic to primary culture cells obtained from metastasis lesions of patients suffering from striated muscle tumors originating in ductus Mulleri and reported to be resistant to all chemotherapic agents.

While particular embodiments of the present invention have been illustrated and described, it would be obvious to those skilled in the art that various other changes and modifications can be made without departing from the spirit and scope of the invention. Therefore, it is intended to cover in the appended claims all such changes and modifications that are within the scope of this invention.

What is claimed as new and desired to be secured by Letters Patent of the United States is:

1. DNA coding the following amino acid sequence (I):

Y—Ala—Asn—Pro—Gln—Ala—Glu—Gly—Gln—Leu—

—Gln—Trp—Leu—Asn—Arg—Arg—Ala—Asn—Ala—

—Leu—Leu—Ala—Asn—Gly—Val—Glu—Leu—Arg—

—Asp—Asn—Gln—Leu—Val—Val—Pro—Ser—Glu—

—Gly—Leu—Tyr—Leu—Ile—Tyr—Ser—Gln—Val—

—Leu—Phe—Lys—Gly—Gln—Gly—Cys—Pro—Ser—

—Thr—His—Val—Leu—Leu—Thr—His—Thr—Ile—

—Ser—Arg—Ile—Ala—Val—Ser—Tyr—Gln—Thr—

—Lys—Val—Asn—Leu—Leu—Ser—Ala—Ile—Lys—

—Ser—Pro—Cys—Gln—Arg—Glu—Thr—Pro—Glu—

—Gly—Ala—Glu—Ala—Lys—Pro—Trp—Tyr—Glu—

—Pro—Ile—Tyr—Leu—Gly—Gly—Val—Phe—Gln—

—Leu—Glu—Lys—Gly—Asp—Arg—Leu—Ser—Ala—

—Glu—Ile—Asn—Arg—Pro—Asp—Tyr—Leu—Asp—

—Phe—Ala—Glu—Ser—Gly—Gln—Val—Tyr—Phe—

—Gly—Ile—Ile—Ala—Leu wherein Y is a peptide selected from the group consisting of:

(1) Met-Val-Lys-Ser-Ser-Thr-Arg-Thr-Pro-Ser-Arg-Lys-Pro-Val-Ala-His-Val-Val;
(2) Met-Val-Arg-Ser-Ser-Thr-Arg-Thr-Pro-Ser-Arg-Lys-Pro-Val-Ala-His-Val-Val; and
(3) Met-Val-Arg-Ser-Cys-Thr-Arg-Thr-Pro-Ser-Arg-Lys-Pro-Val-Ala-His-Val-Val.

2. The DNA of claim 1, wherein the bases of the amino acid before the Ala following Y are TC, the bases of the Ala are GCG, and the first base of the amino acid after the Ala is A.

3. A plasmid which incorporates therein DNA coding the following amino acid sequence (I):

Y—Ala—Asn—Pro—Gln—Ala—Glu—Gly—Gln—Leu—
—Gln—Trp—Leu—Asn—Arg—Arg—Ala—Asn—Ala—
—Leu—Leu—Ala—Asn—Gly—Val—Glu—Leu—Arg—
—Asp—Asn—Gln—Leu—Val—Val—Pro—Ser—Glu—
—Gly—Leu—Tyr—Leu—Ile—Tyr—Ser—Gln—Val—
—Leu—Phe—Lys—Gly—Gln—Gly—Cys—Pro—Ser—
—Thr—His—Val—Leu—Leu—Thr—His—Thr—Ile—
—Ser—Arg—Ile—Ala—Val—Ser—Tyr—Gln—Thr—
—Lys—Val—Asn—Leu—Leu—Ser—Ala—Ile—Lys—
—Ser—Pro—Cys—Gln—Arg—Glu—Thr—Pro—Glu—
—Gly—Ala—Glu—Ala—Lys—Pro—Trp—Tyr—Glu—
—Pro—Ile—Tyr—Leu—Gly—Gly—Val—Phe—Gln—
—Leu—Glu—Lys—Gly—Asp—Arg—Leu—Ser—Ala—
—Glu—Ile—Asn—Arg—Pro—Asp—Tyr—Leu—Asp—
—Phe—Ala—Glu—Ser—Gly—Gln—Val—Tyr—Phe—
—Gly—Ile—Ile—Ala—Leu wherein Y is a peptide selected from the group consisting of:

(1) Met-Val-Lys-Ser-Ser-Thr-Arg-Thr-Pro-Ser-Arg-Lys-Pro-Val-Ala-His-Val-Val;
(2) Met-Val-Arg-Ser-Ser-Thr-Arg-Thr-Pro-Ser-Arg-Lys-Pro-Val-Ala-His-Val-Val; and
(3) Met-Val-Arg-Ser-Cys-Thr-Arg-Thr-Pro-Ser-Arg-Lys-Pro-Val-Ala-His-Val-Val.

4. A process for preparing a polypeptide represented by the following amino acid sequence (I'):

Y'—Ala—Asn—Pro—Gln—Ala—Glu—Gly—Gln—Leu—Gln—
Trp—Leu—Asn—Arg—Arg—Ala—Asn—Ala—Leu—
Leu—Ala—Asn—Gly—Val—Glu—Leu—Arg—Asp—Asn—Gln—
Leu—Val—Val—Pro—Ser—Glu—Gly—Leu—Tyr—Leu—Ile—
Tyr—Ser—Gln—Val—Leu—Phe—Lys—Gly—
Gln—Gly—Cys—Pro—Ser—Thr—His—Val—Leu—Leu—Thr—
His—Thr—Ile—Ser—Arg—Ile—Ala—Val—Ser—Tyr—Gln—
Thr—Lys—Val—Asn—Leu—Leu—Ser—Ala—Ile—Lys—Ser—
Pro—Cys—Gln—Arg—Glu—Thr—Pro—Glu—Gly—Ala—Glu—
Ala—Lys—Pro—Trp—Tyr—Glu—Pro—Ile—Tyr—Leu—Gly—
Gly—Val—Phe—Gln—Leu—Glu—Lys—Gly—Asp—Arg—Leu—
Ser—Ala—Glu—Ile—Asn—Arg—Pro—Asp—Tyr—Leu—Asp—
Phe—Ala—Glu—Ser—Gly—Gln—Val—Tyr—Phe—Gly—Ile—
Ile—Ala—Leu wherein Y' is a peptide selected from the group consisting of:

(1') Val-Lys-Ser-Ser-Thr-Arg-Thr-Pro-Ser-Arg-Lys-Pro-Val-Ala-His-Val-Val;
(2') Val-Arg-Ser-Ser-Thr-Arg-Thr-Pro-Ser-Arg-Lys-Pro-Val-Ala-His-Val-Val; and
(3') Val-Arg-Ser-Cys-Thr-Arg-Thr-Pro-Ser-Arg-Lys-Pro-Val-Ala-His-Val-Val, said process comprising culturing a microorganism which incorporates therein a plasmid capable of growing in the host microorganism and incorporating therein DNA which codes an amino acid sequence corresponding to said amino acid sequence (I') further containing an initiation codon Met.

5. The DNA of claim 1, wherein Y is:

(1) Met-Val-Lys-Ser-Ser-Thr-Arg-Thr-Pro-Ser-Arg-Lys-Pro-Val-Ala-His-Val-Val.

6. The DNA of claim 1, wherein Y is:

(2) Met-Val-Arg-Ser-Ser-Thr-Arg-Thr-Pro-Ser-Arg-Lys-Pro-Val-Ala-His-Val-Val.

7. The DNA of claim 1, wherein Y is:

(3) Met-Val-Arg-Ser-Cys-Thr-Arg-Thr-Pro-Ser-Arg-Lys-Pro-Val-Ala-His-Val-Val.

8. The plasmid of claim 3, wherein Y is:

(1) Met-Val-Lys-Ser-Ser-Thr-Arg-Thr-Pro-Ser-Arg-Lys-Pro-Val-Ala-His-Val-Val.

9. The plasmid of claim 3, wherein Y is:

(2) Met-Val-Arg-Ser-Ser-Thr-Arg-Thr-Pro-Ser-Arg-Lys-Pro-Val-Ala-His-Val-Val.

10. The plasmid of claim 3, wherein Y is:

(3) Met-Val-Arg-Ser-Cys-Thr-Arg-Thr-Pro-Ser-Arg-Lys-Pro-Val-Ala-His-Val-Val.

* * * * *

UNITED STATES PATENT AND TRADEMARK OFFICE
CERTIFICATE OF CORRECTION

PATENT NO. : 5,081,021

DATED : January 14, 1992

INVENTOR(S) : Den'ichi Mizuno, et al.

It is certified that error appears in the above-identified patent and that said Letters Patent is hereby corrected as shown below:

Title page, item [30], add "Foreign Application Priority Data,
    --Jul. 17, 1986 [JP] Japan.......61-169522--.

Signed and Sealed this

First Day of June, 1993

Attest:

MICHAEL K. KIRK

Attesting Officer        Acting Commissioner of Patents and Trademarks